(12) United States Patent
Terranova et al.

(10) Patent No.: US 6,783,557 B1
(45) Date of Patent: Aug. 31, 2004

(54) CATIONIC OXIDATION BASES, THEIR USE FOR THE OXIDATION DYEING OF KERATIN FIBRES, DYEING COMPOSITIONS AND DYEING METHODS

(75) Inventors: Eric Terranova, Bois Colombes (FR); Aziz Fadli, Chelles (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/889,503

(22) PCT Filed: Jan. 14, 2000

(86) PCT No.: PCT/FR00/00073

§ 371 (c)(1),
(2), (4) Date: Oct. 22, 2001

(87) PCT Pub. No.: WO00/43396

PCT Pub. Date: Jul. 27, 2000

(30) Foreign Application Priority Data

Jan. 19, 1999 (FR) .............................. 99 00503

(51) Int. Cl.[7] ................................................ A61K 7/13
(52) U.S. Cl. ..................... 8/405; 8/406; 8/408; 8/407; 8/423; 8/473; 8/567; 8/573; 544/281; 548/360.5
(58) Field of Search ........................... 8/405, 407, 408, 8/409, 567, 573, 406, 423; 544/281; 548/360.5

(56) References Cited

U.S. PATENT DOCUMENTS

| | | | |
|---|---|---|---|
| 4,003,699 A | 1/1977 | Rose et al. | 8/10.2 |
| 4,823,985 A | 4/1989 | Grollier et al. | 222/1 |
| 5,032,137 A | 7/1991 | Junino et al. | 8/410 |
| 6,099,592 A | 8/2000 | Vidal et al. | 8/409 |
| 6,099,593 A | 8/2000 | Terranova et al. | 8/409 |
| 6,248,137 B1 | 6/2001 | Terranova et al. | 8/409 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 926 149 | 1/1999 |
| FR | 2 586 913 | 3/1987 |
| FR | 2 630 438 | 10/1989 |
| FR | 2 733 749 | 11/1996 |
| FR | 2 750 048 | 12/1997 |
| FR | 2 766 178 | 1/1999 |
| WO | WO 97/49378 | * 12/1997 ............ A61K/7/13 |

OTHER PUBLICATIONS

English language Derwent Abstract of DE 38 43 892, Jun. 28, 1990.
English language Derwent Abstract of DE 41 33 957, Apr. 15, 1993.
English language Derwent Abstract of DE 195 43 988, May 28, 1997.
English language Derwent Abstract of FR 2 766 178, Jan. 22, 1999.

* cited by examiner

Primary Examiner—Brian P Mruk
Assistant Examiner—Eisa Elhilo
(74) Attorney, Agent, or Firm—Finnegan, Henderson, Farabow, Garrett & Dunner, L.L.P.

(57) ABSTRACT

The invention concerns novel pyrazolo[1,5-a]pyrimidines comprising at least a cationic group Z, Z being selected among quaternized aliphatic chains, aliphatic chains comprising at least a quaternized cycle, and their use as oxidation base for dyeing keratin fibers, the dyeing compositions containing them, and the oxidation dyeing methods using them.

33 Claims, No Drawings

CATIONIC OXIDATION BASES, THEIR USE FOR THE OXIDATION DYEING OF KERATIN FIBRES, DYEING COMPOSITIONS AND DYEING METHODS

The invention relates to novel pyrazolo[1,5-a] pyrimidines comprising at least one cationic group Z, Z being selected from quaternized aliphatic chains, aliphatic chains containing at least one quaternized saturated ring and aliphatic chains containing at least one quaternized unsaturated ring, to their use as oxidation base for the oxidation dyeing of keratinous fibres, to the dyeing compositions comprising them, and to the methods of oxidation dyeing which employ them.

It is known to dye keratinous fibres, and especially human hair, with dyeing compositions comprising oxidation dye precursors, especially ortho- or para-phenylenediamines, ortho- or para-aminophenols, and heterocyclic compounds such as diaminopyrazole derivatives, which are referred to generally as oxidation bases. The oxidation dye precursors or oxidation bases are colourless or slightly coloured compounds which, when combined with oxidizing products, have the capacity to give rise to coloured and colouring compounds by virtue of a process of oxidative condensation.

It is also known that the shades obtained with these oxidation bases may be varied by combining them with couplers or coloration modifiers, the latter being selected in particular from aromatic meta-diamines, meta-aminophenols, meta-diphenols and certain heterocyclic compounds.

The variety of molecules employed as oxidation bases and couplers makes it possible to obtain a rich palette of colours.

The so-called permanent coloration obtained by virtue of these oxidation dyes is required, moreover, to satisfy acertain number of requirements. Hence it must have no toxicological drawbacks, must allow shades of the desired intensity to be obtained, and must have good resistance to external agents (light, inclement weather, washing, permanent-waving, perspiration and friction).

The dyes must also allow white hair to be covered and, finally, they must be as unselective as possible; in other words, they must allow the smallest possible differences in coloration to be produced over the entire length of a single keratinous fibre, which may indeed be sensitized (i.e. damaged) differently between its tip and its root.

The applicant has now discovered, completely unexpectedly and surprisingly, that new pyrazolo[1,5-a]pyrimidines of formula (I) defined below, comprising at least one cationic group Z, Z being selected from quaternized aliphatic chains, aliphatic chains containing at least one quaternized saturated ring and aliphatic chains containing at least one quaternized unsaturated ring are not only suitable for use as oxidation dye precursors, but also make it possible to obtain dyeing compositions which lead to intense colorations in a wide palette of colours and have excellent properties of resistance to the various treatments which the keratinous fibres may undergo.

It is these discoveries which form the basis of the present invention.

The invention therefore provides, firstly, novel compounds of formula (I) below, and their addition salts with an acid:

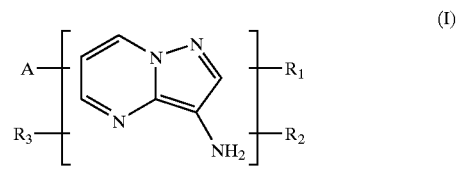

in which:

$R_1$, $R_2$ and $R_3$, which may be identical or different, represent a hydrogen atom; a halogen atom; a group Z; a ($C_1$–$C_6$ alkyl)carbonyl radical; an amino($C_1$–$C_6$ alkyl)carbonyl radical; an N-Z-amino($C_1$–$C_6$ alkyl) carbonyl radical; an N-($C_1$–$C_6$ alkyl)amino($C_1$–$C_6$ alkyl)carbonyl radical; an N,N-di($C_1$–$C_6$ alkyl)amino ($C_1$–$C_6$ alkyl)carbonyl radical; an amino($C_1$–$C_6$ alkyl) carbonyl($C_1$–$C_6$ alkyl) radical; an N-Z-amino($C_1$–$C_6$ alkyl)carbonyl($C_1$–$C_6$ alkyl) radical; an N-($C_1$–$C_6$ alkyl)amino($C_1$–$C_6$ alkyl)carbonyl($C_1$–$C_6$ alkyl) radical; an N,N-di($C_1$–$C_6$ alkyl)amino($C_1$–$C_6$ alkyl)carbonyl($C_1$–$C_6$ alkyl) radical; a carboxyl radical; a ($C_1$–$C_6$ alkyl)carboxyl radical; a ($C_1$–$C_6$ alkyl)sulphonyl radical; an aminosulphonyl radical; an N-Z-aminosulphonyl radical; an N-($C_1$–$C_6$ alkyl)aminosulphonyl radical; an N,N-di($C_1$–$C_6$ alkyl)-aminosulphonyl radical; an aminosulphonyl($C_1$–$C_6$ alkyl) radical; an N-Z-aminosulphonyl($C_1$–$C_6$ alkyl) radical; an N-($C_1$–$C_6$ alkyl)aminosulphonyl($C_1$–$C_6$ alkyl) radical; an N,N-di($C_1$–$C_6$ alkyl)aminosulphonyl ($C_1$–$C_6$ alkyl) radical; a carbamyl radical; an N-($C_1$–$C_6$ alkyl)carbamyl radical; an N,N-di($C_1$–$C_6$ alkyl) carbamyl radical; a carbamyl($C_1$–$C_6$ alkyl) radical; an N-($C_1$–$C_6$ alkyl)carbamyl($C_1$–$C_6$ alkyl) radical; an N,N-di($C_1$–$C_6$ alkyl)carbamyl($C_1$–$C_6$ alkyl) radical; a $C_1$–$C_6$ alkyl radical; a hydroxyl radical; a nitro radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ trifluoroalkyl radical; a cyano radical; a group $OR_6$ or $SR_6$; an amino radical; an N-($C_6$–$C_6$ alkyl)amino radical; an N,N-di($C_1$–$C_6$ alkyl)amino radical (where the two alkyl substituents may form a 5- or 6-membered ring); an N-hydroxy($C_1$–$C_6$ alkyl) amino radical; an N,N-bis(hydroxy($C_1$–$C_6$ alkyl)) amino radical; an N-polyhydroxy($C_2$–$C_6$ alkyl)amino radical; an N,N-bis(polyhydroxy($C_2$–$C_6$ alkyl))amino radical; an amino($C_1$–$C_6$ alkyl)amino radical in which the terminal amino group is unsubstituted or substituted by one or two $C_1$–$C_6$ alkyl radicals, where the said alkyl radicals may form a saturated or unsaturated, 5- or 6-membered ring; an amino group protected by a ($C_1$–$C_6$ alkyl)carbonyl, trifluoro($C_1$–$C_6$ alkyl)carbonyl, amino($C_1$–$C_6$ alkyl)carbonyl, N-Z-amino($C_1$–$C_6$ alkyl)-carbonyl, N-($C_1$–$C_6$ alkyl)amino($C_1$–$C_6$ alkyl) carbonyl, N,N-di($C_1$–$C_6$ alkyl)amino($C_1$–$C_6$ alkyl) carbonyl or formyl radical or by a group Z;

$R_6$ denotes a $C_1$–$C_6$ alkyl radical; a $C_1$–$C_6$ monohydroxyalkyl radical; a $C_2$–$C_6$ polyhydroxyalkyl radical; a group Z; a $C_1$–$C_6$ ($C_1$–$C_6$ alkoxy)alkyl radical; an aryl radical; a benzyl radical; a $C_1$–$C_6$ carboxyalkyl radical; a $C_1$–$C_6$ ($C_1$–$C_6$ alkyl)carboxyalkyl radical; a $C_1$–$C_6$ cyanoalkyl radical; a $C_1$–$C_6$ carbamylalkyl radical; a $C_1$–$C_6$ N-($C_1$–$C_6$ alkyl)carbamylalkyl radical; a $C_1$–$C_6$ N,N-di($C_1$–$C_6$ alkyl)carbamylalkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)aminosulphonylalkyl radical; a $C_1$–$C_6$ N,N-di($C_1$–$C_6$ alkyl)aminosulphonylalkyl radical; a $C_1$–$C_6$ ($C_1$–$C_6$ alkyl)sulphinylalkyl radical; a $C_1$–$C_6$ ($C_1$–$C_6$ alkyl)sulphonylalkyl radical; a $C_1$–$C_6$ ($C_1$–$C_6$ alkyl)carbonylalkyl radical; a $C_1$–$C_6$ aminoalkyl radical; a $C_1$–$C_6$ aminoalkyl radical whose amine is substituted by one or two identical or different radicals selected from $C_1$–$C_6$ alkyl, monohydroxy ($C_1$–$C_6$ alkyl), polyhydroxy($C_2$–$C_6$ alkyl), ($C_1$–$C_6$ alkyl)-carbonyl, formyl, trifluoro($C_1$–$C_6$ alkyl)carbonyl and ($C_1$–$C_6$ alkyl)sulphonyl radicals or by a group Z;

A represents a group —$NR_4R_5$ or a hydroxyl radical;

$R_4$ and $R_5$, which are identical or different, represent a hydrogen atom; a group Z; a $C_1$–$C_6$ alkyl radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; an aryl radical; a benzyl radical; a $C_1$–$C_6$ cyanoalkyl radical; a $C_1$–$C_6$ carbamylalkyl radical; a $C_1$–$C_6$ N-($C_1$–$C_6$ alkyl)carbamylalkyl radical; a $C_1$–$C_6$ N,N-di($C_1$–$C_6$ alkyl)carbamylalkyl radical; a $C_1$–$C_6$ thiocarbamylalkyl radical; a $C_1$–$C_6$ trifluoroalkyl radical; a $C_1$–$C_6$ sulphoalkyl radical; a $C_1$–$C_6$ ($C_1$–$C_6$ alkyl)carboxyalkyl radical; a $C_1$–$C_6$ ($C_1$–$C_6$ alkyl)sulphinylalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)-aminosulphonylalkyl radical; a $C_1$–$C_6$ N,N-di($C_1$–$C_6$ alkyl)aminosulphonylalkyl radical; a $C_1$–$C_6$ ($C_1$–$C_6$ alkyl)carbonylalkyl radical; a $C_1$–$C_6$ aminoalkyl radical; a $C_1$–$C_6$ aminoalkyl radical whose amine is substituted by one or two identical or different radicals selected from $C_1$–$C_6$ alkyl, $C_1$–$C_6$ monohydroxyalkyl, $C_2$–$C_6$ polyhydroxyalkyl, ($C_1$–$C_6$ alkyl)carbonyl, ($C_1$–$C_6$ alkyl)sulphonyl, formyl and trifluoro($C_1$–$C_6$ alkyl)carbonyl radicals or by a group Z; one and only one of the radicals $R_4$ and $R_5$ may also represent a ($C_1$–$C_6$ alkyl)carbonyl; formyl; trifluoro ($C_1$–$C_6$ alkyl)carbonyl; amino($C_1$–$C_6$ alkyl)carbonyl, N-Z-amino ($C_1$–$C_6$ alkyl)carbonyl; N-($C_1$–$C_6$ alkyl)amino($C_1$–$C_6$ alkyl)carbonyl; or N,N-di($C_1$–$C_6$ alkyl)amino($C_1$–$C_6$ alkyl)carbonyl radical;

Z is selected from the unsaturated cationic groups of formulae (II) and (III) below and the saturated cationic groups of formula (IV) below:

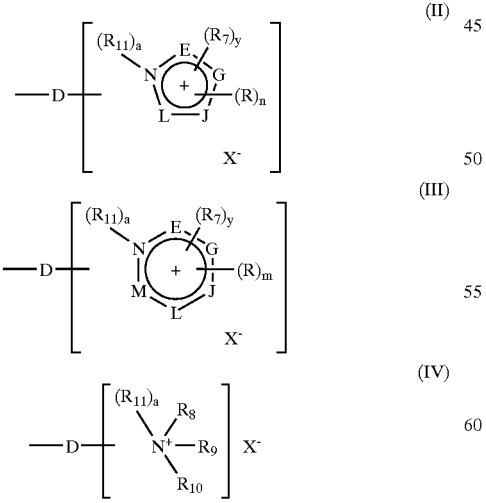

in which:

D is a linker which represents an alkyl chain containing preferably 1 to 14 carbon atoms, is linear or branched and may be interrupted by one or more heteroatoms such as oxygen, sulphur or nitrogen atoms and may be substituted by one or more hydroxyl or $C_1$–$C_6$ alkoxy radicals, and may carry one or more ketone functions;

the ring members E, G, J, L and M, which are identical or different, represent a carbon, oxygen, sulphur or nitrogen atom;

n is an integer between 0 and 4, inclusively;

m is an integer between 0 and 5, inclusively;

the radicals R, which are identical or different, represent a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a $C_1$–$C_6$ tri($C_1$–$C_6$ alkyl)silanealkyl radical, an amido radical, an aldehydo radical, a carboxyl radical, a $C_1$–$C_6$ alkylcarbonyl radical, a thio radical, a $C_1$–$C_6$ thioalkyl radical, a ($C_1$–$C_6$ alkyl)thio radical, an amino radical, an amino radical protected by a ($C_1$–$C_6$ alkyl)carbonyl, carbamyl or ($C_1$–$C_6$ alkyl)sulphonyl radical; a group NHR" or NR"R'" in which R" and R'", which are identical or different, represent a $C_1$–$C_6$ alkyl radical, a $C_1$–$C_6$ monohydroxyalkyl radical or a $C_2$–$C_6$ polyhydroxyalkyl radical;

$R_7$ represents a $C_1$–$C_6$ alkyl radical, a $C_1$–$C_6$ monohydroxyalkyl radical, a $C_2$–$C_6$ polyhydroxyalkyl radical, a $C_1$–$C_6$ cyanoalkyl radical, a $C_1$–$C_6$ tri($C_1$–$C_6$ alkyl)silanealkyl radical, a $C_1$–$C_6$ ($C_1$–$C_6$ alkoxy)alkyl radical, a carbamyl($C_1$–$C_6$ alkyl) radical, a $C_1$–$C_6$ ($C_1$–$C_6$ alkyl)carboxyalkyl radical, a benzyl radical, or a group Z;

$R_8$, $R_9$ and $R_{10}$, which are identical or different, represent a $C_1$–$C_6$ alkyl radical, a $C_1$–$C_6$ monohydroxyalkyl radical, a $C_2$–$C_6$ polyhydroxyalkyl radical, a $C_1$–$C_6$ ($C_1$–$C_6$ alkoxy)alkyl radical, a $C_1$–$C_6$ cyanoalkyl radical, an aryl radical, a benzyl radical, a $C_1$–$C_6$ amidoalkyl radical, a $C_1$–$C_6$ tri($C_1$–$C_6$ alkyl)silanealkyl radical or a $C_1$–$C_6$ aminoalkyl radical whose amine is protected by a ($C_1$–$C_6$ alkyl)carbonyl, amido, carboxyl or ($C_1$–$C_6$ alkyl)sulphonyl radical; two of the radicals $R_8$, $R_9$ and $R_{10}$ may also form, together with the nitrogen atom to which they are attached, a saturated 5- or 6-membered carbon-containing ring or one containing one or more heteroatoms such as, for example, a pyrrolidine ring, a piperidine ring, a piperazine ring or a morpholine ring, it being possible for the said ring to be unsubstituted or substituted by a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a $C_1$–$C_6$ tri($C_1$–$C_6$ alkyl)silanealkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$ alkyl)thio radical, an amino radical, or an amino radical protected by a ($C_1$–$C_6$ alkyl)carbonyl, carbamyl or ($C_1$–$C_6$ alkyl)sulphonyl radical; one of the radicals $R_8$, $R_9$ and $R_{10}$ may also represent a second group Z, identical to or different from the first group Z;

$R_{11}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is protected by a ($C_1$–$C_6$ alkyl)carbonyl or ($C_1$–$C_6$ alkyl)sulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a $C_1$–$C_6$ tri($C_1$–$C_6$ alkyl)silanealkyl radical; a $C_1$–$C_6$ sulphonamidoalkyl radical; a $C_1$–$C_6$ ($C_1$–$C_6$ alkyl)carboxyalkyl radical; a $C_1$–$C_6$ ($C_1$–$C_6$ alkyl)-sulphinylalkyl radical; a $C_1$–$C_6$ ($C_1$–$C_6$ alkyl) sulphonylalkyl radical; a $C_1$–$C_6$ ($C_1$–$C_6$ alkyl)ketoalkyl radical; a $C_1$–$C_6$ N-($C_1$–$C_6$ alkyl)carbamylalkyl radical; a $C_1$–$C_6$ N-($C_1$–$C_6$ alkyl) sulphonamidoalkyl radical;

a and y are integers equal to 0 or 1; with the following conditions:

in the unsaturated cationic groups of formula (II):
when a=0, the linker D is attached to the nitrogen atom,
when a=1, the linker D is attached to one of the ring members E, G, J or L,
y can adopt the value 1 only
1) when the ring members E, G, J and L simultaneously represent a carbon atom and when the radical $R_7$ is carried by the nitrogen atom of the unsaturated ring; or else
2) when at least one of the ring members E, G, J and L represents a nitrogen atom to which the radical $R_7$ is attached;

in the unsaturated cationic groups of formula (III):
when a=0, the linker D is attached to the nitrogen atom,
when a=1, the linker D is attached to one of the ring members E, G, J, L or M,
y can adopt the value 1 only when at least one of the ring members E, G, J, L and M represents a divalent atom and when the radical $R_7$ is carried by the nitrogen atom of the unsaturated ring;

in the cationic groups of formula (IV):
when a=0, then the linker D is attached to the nitrogen atom which carries the radicals $R_8$ to $R_{10}$,
when a=1, then two of the radicals $R_8$ to $R_{10}$, together with the nitrogen atom to which they are attached, form a 5- or 6-membered saturated ring as defined above, and the linker D is carried by a carbon atom of the said saturated ring;

X⁻ represents a monovalent or divalent anion and is selected preferably from a halogen atom such as chlorine, bromine, fluorine or iodine, a hydroxide, a hydrogen sulphate or a $C_1$–$C_6$ alkyl sulphate such as, for example, a methyl sulphate or an ethyl sulphate; with the proviso that the number of cationic groups Z is at least 1.

As indicated above, the colorations obtained with the oxidation dyeing composition in accordance with the invention are intense and make it possible to obtain a wide palette of colours. Moreover, they exhibit excellent properties of resistance with respect to the action of various external agents (light, inclement weather, washing, permanent-waving, perspiration, friction). These properties are particularly remarkable as regards notably, the resistance of the colorations obtained with respect to the action of light, washing, permanent-waving and perspiration.

In the formula (I) above, the alkyl and alkoxy radicals may be linear or branched.

Among the rings of the unsaturated groups Z of formula (II) above, mention may be made in particular, by way of example, of pyrrole, imidazole, pyrazole, oxazole, thiazole and triazole rings.

Among the rings of the unsaturated groups Z of formula (III) above, mention may be made in particular, by way of example, of pyridine, pyrimidine, pyrazine, oxazine and triazine rings.

Among the compounds of formula (I) above, mention may be made in particular of the following:

3-[3-(3-amino-5-methylpyrazolo[1,5-a]pyrimidin-7-ylamino)propyl]-1-(2-hydroxyethyl)-3H-imidazol-1-ium chloride, 3-[(3-aminopyrazolo[1,5-a]pyrimidin-7-ylcarbamoyl)-methyl)-1-methyl-3H-imidazol-1-ium chloride, 3-(3-amino-7-hydroxy-5-methylpyrazolo[1,5-a]-pyrimidin-6-ylmethyl)-1-methylpyridinium methyl sulphate, 3-(3-amino-7-hydroxy-5-methylpyrazolo[1,5-a]-pyrimidin-6-ylmethyl)-1-(2-hydroxyethyl)pyridinium chloride, 2-[(3-aminopyrazolo[1,5-a]pyrimidin-7-ylamino) methyl]-1,3-dimethyl-3H-imidazol-1-ium methyl sulphate, 3-[(3-aminopyrazolo[1,5-a]pyrimidin-7-ylamino)-methyl]-1-methylpyridinium methyl sulphate, 3-[(3-aminopyrazolo[1,5-a]pyrimidin-7-ylamino)-methyl]-1-methylpyridinium methyl sulphate, 2-(3,7-diamino-5-methylpyrazolo[1,5-a]pyrimidin-6-ylmethyl)-1,3-dimethyl-3H-imidazol-1-ium methyl sulphate, 2-(3-amino-7-hydroxy-5-methylpyrazolo[1,5-a]-pyrimidin-6-ylmethyl)-1,3-dimethyl-3H-imidazol-1-ium methyl sulphate, 2-(3,7-diaminopyrazolo[1,5-a]pyrimidin-2-yl)-1-methylpyridinium methyl sulphate,

[3-(3-amino-5-methylpyrazolo[1,5-a]pyrimidin-7-ylamino)propyl]trimethylammonium chloride,

[3-(3-amino-5-methylpyrazolo[1,5-a]pyrimidin-7-ylamino)propyl]trimethylammonium methyl sulphate, 1-[3-(3-amino-5-methylpyrazolo[1,5-a]pyrimidin-7-ylamino)propyl]-1-methylpiperidinium chloride, 1-[3-(3-amino-5-methylpyrazolo[1,5-a]pyrimidin-7-ylamino)propyl]-1-methylpiperidinium methyl sulphate, 4-[3-(3-amino-5-methylpyrazolo[1,5-a]pyrimidin-7-ylamino)propyl]-4-methylmorpholin-4-ium chloride, 4-[3-(3-amino-5-methylpyrazolo[1,5-a]pyrimidin-7-ylamino)propyl]-4-methylmorpholin-4-ium methyl sulphate, and their addition salts with an acid.

Among these compounds of formula (I), more particular preference is given to the following:

3-[3-(3-amino-5-methylpyrazolo[1,5-a]pyrimidin-7-ylamino)propyl]-1-(2-hydroxyethyl)-3H-imidazol-1-ium chloride, 3-(3-amino-7-hydroxy-5-methylpyrazolo[1,5-a]-pyrimidin-6-ylmethyl)-1-methylpyridinium methyl sulphate, 3-(3-amino-7-hydroxy-5-methylpyrazolo[1,5-a]-pyrimidin-6-ylmethyl)-1-(2-hydroxyethyl)pyridinium chloride, 3-(3-amino-7-hydroxy-5-methylpyrazolo[1,5-a]-pyrimidin-6-ylmethyl)-1-methylpyridinium chloride, 4-[3-(3-amino-5-methylpyrazolo[1,5-a]pyrimidin-7-ylamino)propyl]-4-methylmorpholin-4-ium chloride, 4-[3-(3-amino-5-methylpyrazolo[1,5-a]pyrimidin-7-ylamino)propyl]-4-methylmorpholin-4-ium methyl sulphate, and their addition salts with an acid.

The compounds of formula (I) in accordance with the invention may be readily obtained in accordance with well-known methods of the prior art:

firstly by reduction of the corresponding cationic nitroso or nitro compounds. In this case, reduction to the corresponding primary aromatic amine is carried out in accordance with conventional methods (J. Lehmman in Houben-Weyl, "Methoden der Organischen Chemie", volume IV/1c: Reduction 1 page 491 to 537, 1980). The methods which are preferred in accordance with the invention involve metals such as Zn, Sn or Fe in an acidic medium such as aqueous hydrochloric acid or aqueous acetic acid in the presence or absence of a cosolvent such as methanol, ethanol or tetrahydrofuran. Catalytic hydrogenation is a preferred reduction method in accordance with the invention. This catalytic hydrogenation makes use of metals such as palladium, platinum or nickel. More particularly still, preference is given to palladium on carbon or to Raney nickel, or else to oxides such as $PtO_2$ in solvents such as ethanol, ethanol, tetrahydrofuran or ethyl acetate in the presence or absence of an acid such as, for example, acetic acid. These catalytic reductions may also be carried out with formic acid in the presence of a trialkylamine such as triethylamine or with ammonium formate in the place of gaseous hydrogen. (S. Ram, R. E. Ehrenkaufer, Synthesis, 1988,91);

secondly, by reduction of the corresponding cationic azo compounds (reductive cleavage). Reduction to the corresponding primary aromatic amine is carried out in accordance with conventional methods (J. Lehmman in Houben-Weyl, "Methoden der Organischen Chemie", volume IV/1c: Reduction 1 page 551 to 553, 1980; E. C. Taylor et al., J. Amer. Chem. Soc. 80, 421, 1958).

This step of reduction (to obtain a primary aromatic amine), which gives the synthesized compound its character as an oxidizable compound (oxidation base), and is followed or not by formation of a salt, is in general, for convenience, the last step of the synthesis.

This reduction may occur earlier on in the sequence of reactions leading to the preparation of the compounds of formula (I), and in accordance with well-known processes it is then necessary to "protect" the primary amine created (for example by a step of acetylation, benzenesulphonation, etc.), to carry out subsequently the desired substitution(s) or modification(s) (including the quaternization), and to end with the "deprotection" (generally in an acidic medium) of the amine function.

When the synthesis is at an end, the compounds of formula (I) in accordance with the invention may, if appropriate, be recovered by well-known methods of the prior art, such as crystallization or distillation.

The invention additionally provides for the use of the compounds of formula (I) in accordance with the invention as oxidation base for the oxidation dyeing of keratinous fibres and, in particular, of human keratinous fibres such as the hair.

The invention also provides a composition for the oxidation dyeing of keratinous fibres and, in particular, of human keratinous fibres such as the hair, characterized in that it comprises as oxidation base, in a medium appropriate for dyeing, at least one compound of formula (I) in accordance with the invention.

The compound or compounds of formula (I) in accordance with the invention represent(s) preferably from 0.0005 to 12% by weight, approximately, of the total weight of the dyeing composition, and, more preferably still, from 0.005 to 6% by weight, approximately, of this weight.

The medium appropriate for dyeing (or vehicle) generally consists of water or a mixture of water and at least one organic solvent for solubilizing the compounds which would not be sufficiently soluble in water. By way of organic solvent, mention may be made, for example, of $C_1$–$C_4$ lower alkanols, such as ethanol and isopropanol; glycerol; glycols and glycol ethers, such as 2-butoxyethanol, propylene glycol, propylene glycol monomethyl ether, diethylene glycol monoethyl and monomethyl ether, and also aromatic alcohols such as benzyl alcohol or phenoxyethanol, similar products and mixtures thereof.

The solvents may be present in proportions of preferably between 1 and 40% by weight, approximately, relative to the total weight of the dyeing composition, and still more preferably between 5 and 30% by weight, approximately.

The pH of the dyeing composition according to the invention is generally between 3 and 12, approximately, and preferably between 5 and 11, approximately. It may be adjusted to the desired value by means of acidifying or basifying agents which are commonly employed in the dyeing of keratinous fibres.

Among the acidifying agents, mention may be made, by way of example, of mineral acids or organic acids such as hydrochloric acid, orthophosphoric acid, sulphuric acid, carboxylic acids such as acetic acid, tartaric acid, citric acid and lactic acid, and sulphonic acids.

Among the basifying agents, mention may be made, by way of example, of aqueous ammonia, alkali metal carbonates, alkanolamines such as mono-, di- and triethanolamines and their derivatives, sodium hydroxide or potassium hydroxide, and the compounds of formula (V) below:

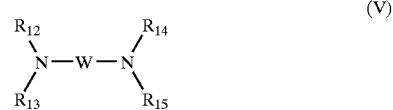

(V)

in which W is a propylene residue optionally substituted by a hydroxyl group or a $C_1$–$C_6$ alkyl radical; and $R_{12}$, $R_{13}$, $R_{14}$ and $R_{15}$, which are identical or different, represent a hydrogen atom or a $C_1$–$C_6$ alkyl or $C_1$–$C_6$ hydroxyalkyl radical.

Furthermore, the dyeing composition according to the invention may comprise, in addition to the dyes defined above, at least one additional oxidation base, which may be selected from the oxidation bases conventionally used in oxidation dyeing and among which mention may be made in particular of para-phenylenediamines, bisphenylalkylenediamines, para-aminophenols; ortho-aminophenols and heterocyclic bases other than the compounds of formula (I).

Among the para-phenylenediamines, mention may be made more particularly, by way of example, of para-phenylenediamine, para-tolylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline, the para-phenylenediamines described in French Patent Application FR 2 630 438, and their addition salts with an acid.

Among the bisphenylalkylenediamines, mention may be made more particularly, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)-ethylenediamine, and their addition salts with an acid.

Among the para-aminophenols, mention may be made more particularly, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their addition salts with an acid.

Among the ortho-aminophenols, mention may be made more particularly, by way of example, of 2-aminophenol, 2-amino-5-methylphenol, 2-amino-6-ethylphenol, 5-acetamido-2-aminophenol, and their addition salts with an acid.

Among the heterocyclic bases, mention may be made more particularly, by way of example, of the pyridine derivatives, the non-cationic pyrimidine derivatives and the pyrazole derivatives.

Among the pyridine derivatives, mention may be made more particularly of the compounds described, for example, in Patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, mention may be made more particularly of the compounds described, roe for example, in German Patent DE 2 359 399 or Japanese Patents JP 88-169 571 and JP 91-10659 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolo-pyrimidine derivatives such as those mentioned in Patent Application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo-[1,5-a]pyrimidin-5-ol; 2-(3-aminopyrazolo[1,5-a]-pyrimidin-7-ylamino)ethanol, 2-(7-aminopyrazolo[1,5-a]-pyrimidin-3-ylamino)ethanol, 2-((3-aminopyrazolo-[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo-[1,5-a]pyrimidine-3,7-diamine, 2,6-dimethylpyrazolo-[1,5-a]pyrimidine-3,7-diamine, 2,5,N7,N7-tetramethylpyrazolo[1,5-a]pyrimidine-3,7-diamine, 3-amino-5-methyl-7-imidazolylpropylamino pyrazolo-[1,5-a]pyrimidine, their addition salts with an acid and their tautomeric forms, when a tautomeric equilibrium exists.

Among the pyrazole derivatives, mention may be made more particularly of the compounds described in Patents DE 3 843 892, DE 4 133 957 and Patent Applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

When they are used, these additional oxidation bases represent preferably from 0.0005 to 12% by weight, approximately, of the total weight of the dyeing composition, and more preferably still from 0.005 to 6% by weight, approximately, of this weight.

The oxidation dyeing compositions according to the invention may also include at least one coupler and/or at least one direct dye, in particular for the purpose of modifying the shades or enriching them with glints.

The couplers which may be used in the oxidation dyeing compositions according to the invention may be selected from the couplers used conventionally in oxidation dyeing, among which mention may be made in particular of meta-phenylenediamines, meta-aminophenols, meta-diphenols and the heterocyclic couplers such as, for example, the indole derivatives, indoline derivatives, pyridine derivatives and pyrazolones, and their addition salts with an acid.

These couplers are selected more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis (2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and their addition salts with an acid.

When they are present, these couplers represent preferably from 0.0001 to 10% by weight, approximately, of the total weight of the dyeing composition, and more preferably still from 0.005 to 5% by weight, approximately, of this weight.

Generally speaking, the addition salts with an acid which may be used in the context of the invention (compounds of formula (I), additional oxidation bases and couplers) are selected in particular from the hydrochlorides, hydrobromides, sulphates, citrates, succinates, tartrates, lactates and acetates.

The dyeing composition in accordance with the invention may also include various adjuvants which are conventionally employed in hair-dyeing compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, penetrants, sequestrants, perfumes, buffers, dispersants, conditioning agents such as, for example, silicones, film-formers, preservatives and opacifiers.

The person skilled in the art will of course take care to select this or these optional complementary compounds such that the advantageous properties intrinsically associated with the oxidation dyeing composition in accordance with the invention are not, or not substantially, adversely affected by the intended addition or additions.

The dyeing composition according to the invention may be presented in a variety of forms, such as in the form of liquids, creams, gels, or in any other form appropriate for carrying out dyeing of keratinous fibres and, in particular, of human hair.

The invention additionally provides a method of dyeing keratinous fibres and, in particular, human keratinous fibres such as the hair, employing the dyeing composition as defined above.

In accordance with this method, at least one dyeing composition as defined above is applied to the fibres, the colour being revealed at an acidic, neutral or alkaline pH with the aid of an oxidizing agent which is added to the dyeing composition right at the time of use or which is present in an oxidizing composition which is applied simultaneously or sequentially, separately.

In accordance with a preferred embodiment of the dyeing method of the invention, the dyeing composition described above is preferably mixed at the time of use with an oxidizing composition comprising, in a medium appropriate for dyeing, at least one oxidizing agent present in an amount sufficient to develop a coloration. The mixture obtained is then applied to the keratinous fibres and is left to act for from approximately 3 to 50 minutes, preferably for from 64 approximately 5 to 30 minutes, after which the fibres are rinsed, washed with shampoo, rinsed again and dried.

The oxidizing agent may be selected from the oxidizing agents which are conventionally used for the oxidation dyeing of keratinous fibres, among which mention may be made of hydrogen peroxide, urea peroxide, alkali metal bromates, persalts such as perborates and persulphates, and enzymes such as peroxidases, laccases, tyrosinases and oxidoreductases, among which mention may be made in particular of the pyranose oxidases, glucose oxidases, glycerol oxidases, lactate oxidases, pyruvate oxidases and uricases.

The pH of the oxidizing composition comprising the oxidizing agent as defined above is such that, after mixing with the dyeing composition, the pH of the resultant composition that is applied to keratinous fibres varies preferably between approximately 3 and 12, and more preferably still between 5 and 11. It is adjusted to the desired value by means of acidifying or basifying agents which are commonly employed in dyeing keratinous fibres, such agents being as defined above.

The oxidizing composition as defined above may also include various adjuvants which are conventionally used in hair-dyeing compositions, such adjuvants being as defined above.

The composition which is ultimately applied to the keratinous fibres may be presented in various forms, such as in the form of liquids, creams or gels or in any other form appropriate for carrying out dyeing of keratinous fibres and, in particular, of human hair.

The invention also provides a multi-compartment dyeing device or "kit", or any other packaging system having two or more compartments, of which a first compartment contains the dyeing composition as defined above and a second compartment contains the oxidizing composition as defined above. These devices may be equipped with a means allowing the desired mixture to be delivered to the hair, such as the devices described in Patent FR-2 586 913 in the name of the applicant.

The examples which follow are intended to illustrate the invention without limiting its scope.

PREPARATION EXAMPLES

Preparation Example 1

Synthesis of 3-[3-(3-amino-5-methylpyrazolo[1,5-a]pyrimidin-7-ylamino)propyl]-1-(2-hydroxyethyl)-3H-imidazol-1-ium dihydrochloride

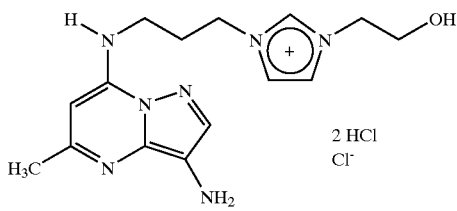

A) Preparation of 3-nitro-5-methylpyrazolo[1,5-a]pyrimidin-7-ol

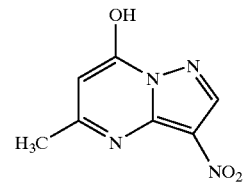

50 g of 4-nitro-2H-pyrazol-3-ylamine hydrochloride (prepared in accordance with H. Dorn and H. Dilcher, Liebigs Ann. Chem., 707, 141, 1967) and 60 g of ethyl acetoacetate in 160 cc of acetic acid were introduced into a 500 cc three-necked round-bottomed flask equipped with a magnetic stirrer, a thermometer and a condenser. The reaction medium was refluxed for 12 hours. The precipitate which formed was filtered off at about 90° C. It was washed with diisopropyl ether and dried under vacuum over phosphoric anhydride. This gave 50 g of 3-nitro-5-methylpyrazolo[1,5-a]pyrimidin-7-ol in the form of yellow crystals (yield=84.5%; melting point=290° C. with decomposition), whose elemental analysis, calculated for $C_7H_6N_4O_3$ (MW=194.15 g), was as follows:

| %          | C     | H    | N     | O     |
|------------|-------|------|-------|-------|
| Calculated | 43.31 | 3.12 | 28.86 | 24.72 |
| Found      | 43.12 | 3.11 | 28.77 | 24.65 | b) Preparation of 7-chloro-5-methyl-3-nitropyrazolo-[1,5-a]pyrimidine

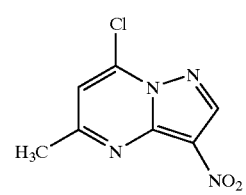

230 cc of phosphorus oxychloride, 15.4 g of N,N-dimethylaniline and 23.3 g of 3-amino-5-methylpyrazolo[1,5-a]pyrimidin-7-ol were introduced into a 500 cc three-necked flask equipped with a magnetic stirrer, a thermometer and a condenser. The reaction medium was refluxed for 2.5 h. Following evaporation of the phosphorus oxychloride under reduced pressure, a highly viscous green oil was obtained to which approximately 400 g of ice were added. A brown solid precipitated. After 30 minutes of stirring, the precipitate was filtered off and washed with petroleum ether and then with diisopropyl ether. Drying under vaccum over phosphoric anhydride gave 21.4 g of 7-chloro-5-methyl-3-nitropyrazolo[1,5-a]pyrimidine in the form of a brown solid with a yield of 83.9%.

c) Preparation of (3-imidazol-1-ylpropyl)(5-methyl-3-nitropyrazolo[1,5-a]pyrimidin-7-yl)amine

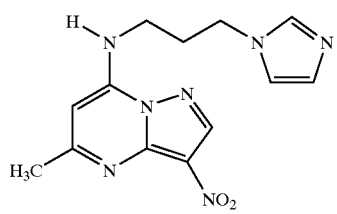

2.88 g of 3-imidazol-1-ylpropylamine and 2.33 g of triethylamine in 20 cc of dioxane were introduced into a 100 cc three-necked round-bottomed flask equipped with a magnetic stirrer, a thermometer, a dropping funnel and a condenser. 4.5 g of 7-chloro-5-methyl-3-nitropyrazolo[1,5-a] pyrimidine in solution in 20 cc of dioxane and 5 cc of dimethylformamide were added dropwise. After 2 hours of stirring at room temperature, the precipitate was filtered off. It was washed with diisopropyl ether and dried under vacuum. This gave 7.2 g of crude product. This product was taken up under reflux in 28 cc of water, then filtered off at room temperature. This operation was repeated a second time. The product was washed with ethanol and with diisopropyl ether. This gave 4.1 g of (3-imidazol-1-ylpropyl)(5-methyl-3-nitropyrazolo[1,5-a]pyrimidin-7-yl)amine in the form of a beige powder, after drying under vacuum over phosphoric anhydride, with a yield of 65%.

d) Preparation of 1-(2-hydroxyethyl)-3-[3-(5-methyl-3-nitropyrazolo[1,5-a]pyrimidin-7-ylamino)propyl]-3H-imidazol-1-ium chloride

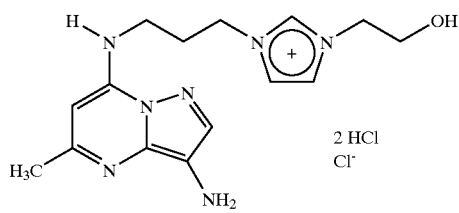

3 g of (3-imidazol-1-ylpropyl)(5-methyl-3-nitropyrazolo [1,5-a]pyrimidin-7-yl)amine and 10 g of 2-chloroethanol were introduced into a 25 cc three-necked round-bottomed flask equipped with a magnetic stirrer, a thermometer and a condenser. The medium was refluxed for 6 hours. The reaction medium was poured into 160 cc of ethyl acetate and refluxed. The precipitate was filtered off at room temperature. This gave 3.8 g of 1-(2-hydroxyethyl)-3-[3-(5-methyl-3-nitropyrazolo[1,5-a]pyrimidin-7-ylamino)propyl]-3H-imidazol-1-ium chloride (beige powder) after drying under vacuum over phosphoric anhydride.

e) Preparation of 3-[3-(3-amino-5-methylpyrazolo-[1,5-a] pyrimidin-7-ylamino)propyl]-1-(2-hydroxyethyl)-3H-imidazol-1-ium chloride dihydrochloride 3.5 g of 1-(2-hydroxyethyl)-3-[3-(5-methyl-3-nitropyrazolo[1,5-a]pyrimidin-7-ylamino)propyl]-3H-imidazol-1-ium chloride in 150 cc of ethanol and then 0.39 g of 5% palladium on carbon (containing 50% water) were introduced into a 250 cc hydrogenator. Between 11 and 12 bars' pressure of hydrogen were introduced into the reactor and the reaction medium was brought to 60° C. After 4 hours of reaction, the catalyst was filtered over Celite and a stream of gaseous hydrochloric acid was passed through the filtrate. The reaction medium was poured into 100 cc of diisopropyl ether. After stirring, the precipitate was filtered off. It was washed with diisopropyl ether and dried under vacuum over phosphoric anhydride. This gave 3.3 g of a highly hygroscopic product. A 3% aqueous solution of this product was formed, and was lyophilized. The resulting solid was taken up at reflux in 30 cc of absolute ethanol. This gives 2.25 g of 3-[3-(3-amino-5-methylpyrazolo[1,5-a]pyrimidn-7-ylamino)propyl]-1-(2-hydroxyethyl)-3H-imidazol-1-ium chloride in the form of the dihydrochloride, after drying under vacuum over phosphoric anhydride, with a yield of 85%, whose analysis calculated for $C_{15}H_{22}N_7OCl$, 2HCl (MW=424.76 g) was as follows:

| % | C | H | N | O | Cl |
|---|---|---|---|---|---|
| Calculated | 42.42 | 5.70 | 23.08 | 3.77 | 25.04 |
| Found | 40.28 | 6.19 | 21.40 | 7.99 | 24.14 |
| Calculated with 1 mol of water | 40.69 | 5.92 | 22.14 | 7.23 | 24.02 |

Preparation Example 2

Synthesis of 3-(3-amino-7-hydroxy-5-methylpyrazolo[1,5-a]pyrimidin-6-ylmethyl)-1-(2-hydroxyethyl)pyridinium chloride, hydrochloride

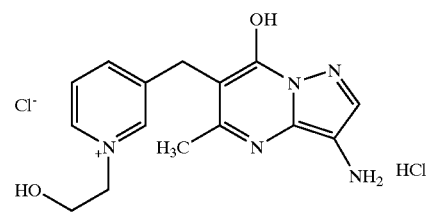

a) Preparation of the Methyl Ester of 3-oxo-2-pyridin-3-ylmethylbutyric acid

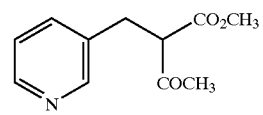

25 g of the methyl ester of 2-acetyl-3-pyridin-3-ylacrylic acid (prepared in accordance with I. Adachi et al., Chem. Pharm. Bull. 35(8), 3235, 1987), 200 cc of ethanol and 5.25 g of 5% palladium on carbon (containing 50% water) were introduced into a 300 cc hydrogenation reactor. A hydrogen pressure of 6 bars was introduced and the reduction was carried out at ambient temperature. The reaction medium was treated when there was no longer any absorption of hydrogen. The catalyst was filtered off and the solvent was evaporated. This gave 24 g of crude product which was treated with 200 cc of diethyl ether. The white precipitate was filtered off and the solvent was evaporated. This gave 20 g of the methyl ester of 3-oxo-2-pyridin-3-ylmethylbutyric acid in the form of a brown oil, with a yield of 79%.

b) Preparation of 5-methyl-3-nitro-6-pyridin-3-yl-methylpyrazolo[1,5-a]pyrimidin-7-ol hydrochloride

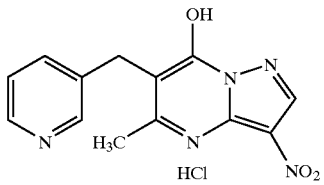

89 g of 4-nitro-2H-pyrazol-3-ylamine (prepared in accordance with H. Dorm and H. Dilcher, Liebigs Ann. Chem., 707, 141, 1967) and 112 g of the methyl ester of 3-oxo-2-pyridin-3-ylmethylbutyric acid, obtained above in the preceding step, in 1120 cc of acetic acid were introduced into a 2-liter three-necked round-bottomed flask equipped with a magnetic stirrer, a thermometer and a condenser. The reaction medium was refluxed for 5 hours. The precipitate which formed was filtered off at room temperature. It was rinsed with diisopropyl ether and dried under vacuum over phosphoric anhydride. This gave 120 g of crude product. This was recrystallized from a water/acetone (1/25) mixture. This gave 77 g of 5-methyl-3-nitro-6-pyridin-3-ylmethylpyrazolo [1,5-a]pyrimidin-7-ol hydrochloride in the form of yellow crystals (yield=50%), whose elemental analysis calculated for $C_{13}H_{11}N_5O_3 \cdot HCl$ was as follows:

| % | C | H | N | O | Cl |
|---|---|---|---|---|---|
| Calculated | 48.53 | 3.76 | 21.77 | 14.92 | 11.02 |
| Found | 48.31 | 3.82 | 21.89 | 14.23 | 11.75 | c) Preparation of 5-methyl-3-nitro-6-pyridin-3-yl-methylpyrazolo[1,5-a]pyrimidin-7-ol

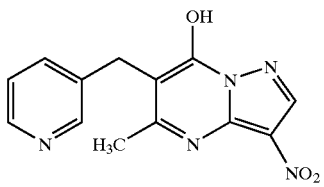

250 cc of water and 10.6 g of 20% aqueous ammonia were introduced into a 500-cc Erlenmeyer flask equipped with a magnetic stirrer. 20 g of 5-methyl-3-nitro-6-pyridin-3-ylmethylpyrazolo[1,5-a]pyrimidin-7-ol hydrochloride were added in solid portions. The reaction mixture was left with stirring at room temperature for 3 hours. The resulting solid was filtered off and then washed with 100 cc of water and then with diisopropyl ether. The product was dried over phosphoric anhydride. This gave 16 g of 5-methyl-3-nitro-6-pyridin-3-ylmethylpyrazolo[1,5-a]pyrimidin-7-ol with a yield of 90%.

d) Preparation of 1-(2-hydroxyethyl)-3-(7-hydroxy-5-methyl-3-nitropyrazolo[1,5-a]pyrimidin-6-ylmethyl)-pyridinium chloride

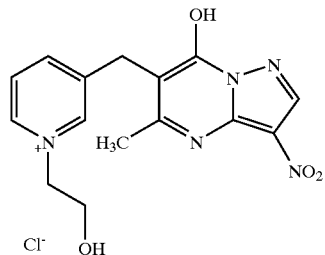

10 g of 5-methyl-3-nitro-6-pyridin-3-yl-methylpyrazolo [1,5-a]pyrimidin-7-ol, obtained above in the preceding step, and 100 cc of 2-chloroethanol were introduced into a 250-cc three-necked round-bottomed flask equipped with a magnetic stirrer, a thermometer and a condenser. The medium was refluxed for 5 hours. The solvent was evaporated and then the product was treated with ethanol. The precipitate was filtered off at room temperature. This gave 10 g of crude product. It was recrystallized from acetic acid. This gave 6.7 g of 1-(2-hydroxyethyl)-3-(7-hydroxy-5-methyl-3-nitropyrazolo[1,5-a]pyrimidin-6-ylmethyl)pyridinium chloride after drying under vacuum over phosphoric anhydride (yield=52%), whose elemental analysis calculated for $C_{15}H_{16}N_5O_4 \cdot Cl$ with 0.28 mol of acetic acid was as follows:

| % | C | H | N | O | Cl |
|---|---|---|---|---|---|
| Calculated | 48.80 | 4.47 | 18.29 | 19.07 | 9.28 |
| Found | 47.69 | 4.56 | 18.26 | 18.85 | 9.51 | e) Preparation of 3-(3-amino-7-hydroxy-5-methylpyrazolo [1,5-a]pyrimidin-6-ylmethyl)-1-(2-hydroxyethyl) pyridinium chloride, hydrochloride 2 g of 1-(2-hydroxyethyl)-3-(7-hydroxy-5-methyl-3-nitropyrazolo[1,5-a]pyrimidin-6-ylmethyl)-pyridinium chloride obtained above in the preceding step in 200 cc of acetic acid and then 0.6 g of 5% palladium on carbon (containing 50% water) were introduced into a 500 cc hydrogenator. 8 bars of hydrogen pressure were introduced into the reactor and the reaction medium was brought to 50° C. After reaction for 3 hours, the catalyst was filtered off over Celite. The solvent was evaporated and the crude product obtained was taken up in 10 cc of 7M hydrochloric ethanol. The precipitate was filtered off. It was washed with diisopropyl ether and dried under vacuum over phosphoric anhydride. This gave 2.7 g of 3-(3-amino-7-hydroxy-5-methylpyrazolo[1,5-a]pyrimidin-6-yl-methyl)-1-(2-hydroxyethyl)pyridinium chloride (a highly hygroscopic product) in the form of the hydrochloride, after drying under vacuum over phosphoric anhydride, with a yield of 75% and an analysis, calculated for $C_{15}H_{18}N_5O_2Cl \cdot HCl$, which was as follows:

| % | C | H | N | O | Cl |
|---|---|---|---|---|---|
| Calculated | 48.40 | 5.14 | 18.81 | 8.60 | 19.05 |
| Found | 47.04 | 5.25 | 17.59 | 10.26 | 18.40 |
| Calculated with 0.5 mol of water | 47.20 | 5.24 | 18.34 | 10.48 | 18.61 |

Application Examples

Examples 1 to 7 of Dyeing in a Basic Medium

The following dyeing compositions (amounts in grams) were prepared:

| EXAMPLE | 1 | 2 | 3 | 4 | 5 | 6 | 7 |
|---|---|---|---|---|---|---|---|
| 3-[3-(3-Amino-5-methylpyrazolo[1,5-a]-pyrimidin-7-ylamino)propyl]-1-(2-hydroxy-ethyl)-3H-imidazol-1-ium chloride dihydro-chloride (oxidation base of formula (I)) | 1.27 | 1.27 | 1.27 | 1.27 | 1.27 | 1.27 | 1.27 |
| 1,3-Dihydroxybenzene (coupler) | — | 0.33 | — | — | — | — | — |
| 3-Aminophenol (coupler) | — | — | 0.327 | — | — | — | — |
| 5-N-(β-Hydroxyethyl)amino 2-methylphenol (coupler) | — | — | — | 0.504 | — | — | — |
| 2,4-Diamino 1-(β-hydroxyethyloxy)benzene, 2HCl (coupler) | — | — | — | — | 0.723 | — | — |
| 6-Hydroxyindole (coupler) | — | — | — | — | — | 0.399 | — |
| 4-Hydroxyindole (coupler) | — | — | — | — | — | — | 0.399 |
| Common dyeing vehicle 1 | (*) | (*) | (*) | (*) | (*) | (*) | (*) |
| Demineralized water q.s. | 100 g | 100 g | 100 g | 100 g | 100 g | 100 g | 100 g |

| (*) Common dyeing vehicle 1: | |
|---|---|
| 96° ethyl alcohol | 18 g |
| Sodium metabisulphite in 35% aqueous solution | 0.68 g |
| Pentasodium salt of diethylenetriaminepentaacetic acid | 1.1 g |
| 20% aqueous ammonia | 10.0 g |

Each of the above dyeing compositions was mixed at the time of use, weight for weight, with a 20-volume hydrogen peroxide solution (6% by weight) with a pH of 3.

The mixture obtained was applied to locks of permed grey hair containing 90% white hair, for 30 minutes. The locks were subsequently rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | iridescent dark blonde |
| 2 | 10 ± 0.2 | coppery red |
| 3 | 10 ± 0.2 | purple mahogany |
| 4 | 10 ± 0.2 | red copper |
| 5 | 10 ± 0.2 | deep violet irridescent light chestnut |
| 6 | 10 ± 0.2 | natural chestnut |
| 7 | 10 ± 0.2 | deep red irridescent |

Examples 8 to 14 of Dyeing in a Neutral Medium

The following dyeing compositions (amounts in grams) were prepared:

| EXAMPLE | 8 | 9 | 10 | 11 | 12 | 13 | 14 |
|---|---|---|---|---|---|---|---|
| 3-[3-(3-Amino-5-methylpyrazolo[1,5-a]-pyrimidin-7-ylamino)propyl]-1-(2-hydroxy-ethyl)-3H-imidazol-1-ium chloride dihydro-chloride (oxidation base of formula (I)) | 1.27 | 1.27 | 1.27 | 1.27 | 1.27 | 1.27 | 1.27 |
| 1,3-Dihydroxybenzene (coupler) | — | 0.33 | — | — | — | — | — |
| 3-Aminophenol (coupler) | — | — | 0.327 | — | — | — | — |
| 5-N-(β-Hydroxyethyl)amino 2-methylphenol (coupler) | — | — | — | 0.504 | — | — | — |
| 2,4-Diamino 1-(β-hydroxyethyloxy)benzene, 2HCl (coupler) | — | — | — | — | 0.723 | — | — |
| 6-Hydroxyindole (coupler) | — | — | — | — | — | 0.399 | — |
| 4-Hydroxyindole (coupler) | — | — | — | — | — | — | 0.399 |
| Common dyeing vehicle 2 | () | () | () | () | () | () | (**) |
| Demineralized water q.s. | 100 g | 100 g | 100 g | 100 g | 100 g | 100 g | 100 g |

| (**) Common dyeing vehicle 2: | |
|---|---|
| 96° ethanol | 18 g |
| $K_2HPO_4/KH_2PO_4$ (1.5 M/1 M) buffer | |
| Sodium metabisulphite | 10 g |
| Pentasodium salt of diethylenetriaminepentaacetic acid | 0.68 g |

Each of the above dyeing compositions was mixed at the time of use, weight for weight, with a 20-volume hydrogen peroxide solution (6% by weight) with a pH of 3.

The mixture obtained was applied to locks of natural grey hair containing 90% white hair, for 30 minutes. The locks were subsequently rinsed, washed with a standard shampoo, rinsed again and then dried.

The shades obtained are given in the table below:

| EXAMPLE | Dyeing pH | Shade obtained |
|---|---|---|
| 8 | 5.7 ± 0.2 | coppery iridescent blonde |
| 9 | 5.7 ± 0.2 | beige light ash blonde |
| 10 | 5.7 ± 0.2 | coppery brown dark blonde |
| 11 | 5.7 ± 0.2 | coppery dark blonde |
| 12 | 5.7 ± 0.2 | purplish red |
| 13 | 5.7 ± 0.2 | natural dark ash blonde |
| 14 | 5.7 ± 0.2 | reddish purple |

What is claimed is:

1. At least one chemical chosen from compounds of formula (I), and acid-addition salt thereof:

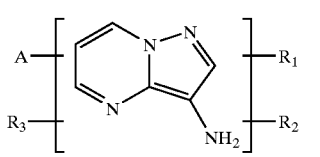

(I)

in which:

$R_1$, $R_2$ and $R_3$, which may be identical or different, are each chosen from a hydrogen atom; a halogen atom; a group Z; a ($C_1$–$C_6$ alkyl)carbonyl radical; an amino ($C_1$–$C_6$ alkyl)carbonyl radical; an N-Z-amino($C_1$–$C_6$ alkyl)carbonyl radical; an N-($C_1$–$C_6$ alkyl)amino ($C_1$–$C_6$ alkyl)carbonyl radical; an N,N-di($C_1$–$C_6$ alkyl) amino($C_1$–$C_6$ alkyl)carbonyl radical; an amino($C_1$–$C_6$ alkyl)carbonyl($C_1$–$C_6$ alkyl) radical; an N-Z-amino ($C_1$–$C_6$ alkyl)carbonyl($C_1$–$C_6$ alkyl) radical; an N-($C_1$–$C_6$ alkyl)amino($C_1$–$C_6$ alkyl)carbonyl($C_1$–$C_6$ alkyl) radical; an N,N-di($C_1$–$C_6$ alkyl)amino($C_1$–$C_6$ alkyl)carbonyl($C_1$–$C_6$ alkyl) radical; a carboxyl radical; a ($C_1$–$C_6$ alkyl)carboxyl radical; a ($C_1$–$C_6$ alkyl) sulphonyl radical; an aminosulphonyl radical; an N-Z-aminosulphonyl radical; an N-($C_1$–$C_6$ alkyl) aminosulphonyl radical; an N,N-di($C_1$–$C_6$ alkyl) aminosulphonyl radical; an aminosulphonyl($C_1$–$C_6$ alkyl) radical; an N-Z-aminosulphonyl($C_1$–$C_6$ alkyl) radical; an N-($C_1$–$C_6$ alkyl)aminosulphonyl($C_1$–$C_6$ alkyl) radical; an N,N-di($C_1$–$C_6$ alkyl)aminosulphonyl ($C_1$–$C_6$ alkyl) radical; a carbamyl radical; an N-($C_1$–$C_6$ alkyl)carbamyl radical; an N,N-di($C_1$–$C_6$ alkyl)carbamyl radical; a carbamyl($C_1$–$C_6$ alkyl) radical; an N-($C_1$–$C_6$ alkyl)carbamyl($C_1$–$C_6$ alkyl) radical; an N,N-di($C_1$–$C_6$ alkyl)carbamyl($C_1$–$C_6$ alkyl) radical; a $C_1$–$C_6$ alkyl radical; a hydroxyl radical; a nitro radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ trifluoroalkyl radical; a cyano radical; a group $OR_6$; a group $SR_6$; an amino radical; an N-($C_1$–$C_6$ alkyl)amino radical; an N,N-di($C_1$–$C_6$ alkyl) amino radical, wherein the two alkyl substituents may form a ring chosen from 5- and 6-membered rings; an N-hydroxy($C_1$–$C_6$ alkyl)amino radical; an N,N-bis (hydroxy($C_1$–$C_6$ alkyl))amino radical; an N-polyhydroxy($C_2$–$C_6$ alkyl)amino radical; an N,N-bis (polyhydroxy($C_2$–$C_6$ alkyl))amino radical; an amino ($C_1$–$C_6$ alkyl)amino radical, in which the terminal amino group is unsubstituted or substituted by one or two $C_1$–$C_6$ alkyl radicals, where the alkyl radicals may form a ring chosen from saturated and unsaturated 5- and 6-membered rings; an amino group protected by at least one group chosen from a ($C_1$–$C_6$ alkyl)carbonyl, a trifluoro($C_1$–$C_6$ alkyl)carbonyl, an amino($C_1$–$C_6$ alkyl)carbonyl, an N-Z-amino($C_1$–$C_6$ alkyl)carbonyl, an N-($C_1$–$C_6$ alkyl)amino($C_1$–$C_6$ alkyl)carbonyl, an N,N-di($C_1$–$C_6$ alkyl)amino($C_1$–$C_6$ alkyl)carbonyl radical, an N,N-di($C_1$–$C_6$ alkyl)amino($C_1$–$C_6$ alkyl) formyl radical, and a group Z;

$R_6$ is chosen from a $C_1$–$C_6$ alkyl radical; a $C_1$–$C_6$ monohydroxyalkyl radical; a $C_2$–$C_6$ polyhydroxyalkyl radical; a group Z; a $C_1$–$C_6$ ($C_1$–$C_6$ alkoxy)alkyl radical; an aryl radical; a benzyl radical; a $C_1$–$C_6$ carboxyalkyl radical; a $C_1$–$C_6$ ($C_1$–$C_6$ alkyl)carboxyalkyl radical; a $C_1$–$C_6$ cyanoalkyl radical; a $C_1$–$C_6$ carbamylalkyl radical; a $C_1$–$C_6$ N-($C_1$–$C_6$ alkyl)carbamylalkyl radical; a $C_1$–$C_6$ N,N-di($C_1$–$C_6$ alkyl)carbamylalkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)aminosulphonylalkyl radical; a $C_1$–$C_6$ N,N-di($C_1$–$C_6$ alkyl) aminosulphonylalkyl radical; a $C_1$–$C_6$ ($C_1$–$C_6$ alkyl) sulphinylalkyl radical; a $C_1$–$C_6$ ($C_1$–$C_6$ alkyl) sulphonylalkyl radical; a $C_1$–$C_6$ ($C_1$–$C_6$ alkyl) carbonylalkyl radical; a $C_1$–$C_6$ aminoalkyl radical; a $C_1$–$C_6$ aminoalkyl radical whose amine is substituted by one or two radicals chosen from $C_1$–$C_6$ alkyl, monohydroxy($C_1$–$C_{76}$ alkyl), polyhydroxy($C_2$–$C_6$ alkyl), ($C_1$–$C_6$ alkyl)carbonyl, formyl, trifluoro($C_1$–$C_6$ alkyl)carbonyl, and ($C_1$–$C_6$ alkyl)sulphonyl radicals, and a group Z;

A is chosen from —$NR_4R_5$ and a hydroxyl radical;

$R_4$ and $R_5$, are independently chosen from a hydrogen atom; a group Z; a $C_1$–$C_6$ alkyl radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; an aryl radical; a benzyl radical; a $C_1$–$C_6$ cyanoalkyl radical; a $C_1$–$C_6$ carbamylalkyl radical; a $C_1$–$C_6$ N-($C_1$–$C_6$ alkyl) carbamylalkyl radical; a $C_1$–$C_6$ N,N-di($C_1$–$C_6$ alkyl) carbamylalkyl radical; a $C_1$–$C_6$ thiocarbamylalkyl radical; a $C_1$–$C_6$ trifluoroalkyl radical; a $C_1$–$C_6$ sulphoalkyl radical; a $C_1$–$C_6$ ($C_1$–$C_6$ alkyl)carboxyalkyl radical; a $C_1$–$C_6$ ($C_1$–$C_6$ alkyl)sulphinylalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)-aminosulphonylalkyl radical; a $C_1$–$C_6$ N,N-di ($C_1$–$C_6$ alkyl)aminosulphonylalkyl radical; a $C_1$–$C_6$ ($C_1$–$C_6$ alkyl)carbonylalkyl radical; a $C_1$–$C_6$ aminoalkyl radical; and a $C_1$–$C_6$ aminoalkyl radical whose amine is substituted by one or two radicals chosen from $C_1$–$C_6$ alkyl, $C_1$–$C_6$ monohydroxyalkyl, $C_2$–$C_6$ polyhydroxyalkyl, ($C_1$–$C_6$ alkyl)carbonyl, ($C_1$-alkyl)

sulphonyl, formyl, and trifluoro($C_1$–$C_6$ alkyl)carbonyl radicals, and a group Z;

wherein one and only one of the radicals $R_4$ and $R_5$ may also be chosen from a ($C_1$–$C_6$ alkyl)carbonyl radical; a formyl radical; a trifluoro($C_1$–$C_6$ alkyl)carbonyl radical; an amino($C_1$–$C_6$ alkyl)carbonyl radical; an N-Z-amino($C_1$–$C_6$ alkyl)carbonyl radical; an N-($C_1$–$C_6$ alkyl)amino($C_1$–$C_6$ alkyl)carbonyl radical; and an N,N-di($C_1$–$C_6$ alkyl)amino($C_1$–$C_6$ alkyl)carbonyl radical;

Z is chosen from the unsaturated cationic groups of formulae (II) and (III) below and the saturated cationic groups of formula (IV) below:

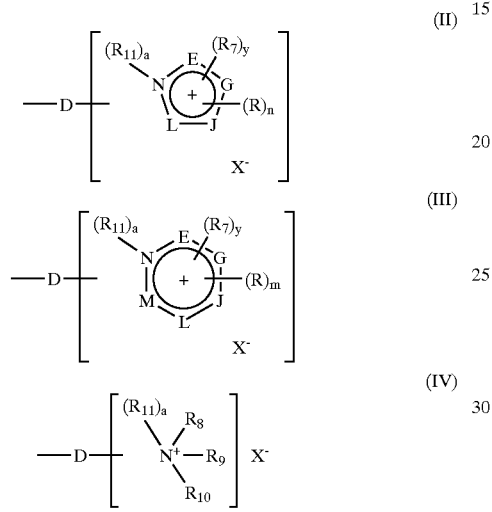

in which:

D is a linker which is chosen from linear and branched alkyl chains and may be interrupted by at least one heteroatom atom and may be substituted by at least one of a hydroxyl and a $C_1$–$C_6$ alkoxy radical, and may carry at least one ketone function;

the ring members E, G, J, L and M, which are identical or different, are chosen from carbon, oxygen, sulphur and nitrogen atoms;

n is an integer ranging from 0 to 4;

m is an integer ranging from 0 to 5;

the radicals R, which are identical or different, may be chosen from a group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a $C_1$–$C_6$ tri($C_1$–$C_6$ alkyl)silanealkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$ alkyl)thio radical; an amino radical; an amino radical protected by a group chosen from ($C_1$–$C_6$ alkyl)carbonyl, carbamyl, and ($C_1$–$C_6$ alkyl)sulphonyl; and groups NHR" and NR"R'" in which R' and R'", which are identical or different, are chosen from a $C_1$–$C_6$ alkyl radical, a $C_1$–$C_6$ monohydroxyalkyl radical and a $C_2$–$C_6$ polyhydroxyalkyl radical;

$R_7$ is chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ cyanoalkyl radical; a $C_1$–$C_6$ tri($C_1$–$C_6$ alkyl)silanealkyl radical; a $C_1$–$C_6$ ($C_1$–$C_6$ alkoxy)alkyl radical; a carbamyl($C_1$–$C_6$ alkyl) radical; a $C_1$–$C_6$ ($C_1$–$C_6$ alkyl)carboxyalkyl radical; a benzyl radical; and a group Z;

$R_8$, $R_9$ and $R_{10}$, which are identical or different, are chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ cyanoalkyl radical; an aryl radical; a benzyl radical; a $C_1$–$C_6$ amidoalkyl radical; a $C_1$–$C_6$ tri($C_1$–$C_6$ alkyl)silanealkyl radical; and a $C_1$–$C_6$ aminoalkyl radical whose amine is protected by at least one of a ($C_1$–$C_6$ alkyl)carbonyl, amido, carboxyl and ($C_1$–$C_6$ alkyl)sulphonyl radical;

two of the radicals $R_8$, $R_9$ and $R_{10}$ may form, together with the nitrogen to which they are attached, a ring chosen from saturated 5- and 6-membered carbon-containing rings which may contain at least one heteroatom, wherein said rings may contain a substituent chosen from a halogen atom; a hydroxyl radical; a $C_1$–$C_6$ alkyl radical, a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a $C_1$–$C_6$ tri($C_1$–$C_6$ alkyl)silanealkyl radical; an amido radical; an aldehydo radical; a carboxyl radical; a $C_1$–$C_6$ ketoalkyl radical; a thio radical; a $C_1$–$C_6$ thioalkyl radical; a ($C_1$–$C_6$ alkyl)thio radical; an amino radical; and an amino radical protected by a group chosen from ($C_1$–$C_6$ alkyl)carbonyl; carbamyl and ($C_1$–$C_6$ alkyl)sulphonyl radical;

one of the radicals $R_8$, $R_9$ and $R_{10}$ may be chosen from a second group Z, identical to or different from the first group Z;

$R_{11}$ may be chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is protected by at least one of a ($C_1$–$C_6$ alkyl) carbonyl, a carbamyl, and a ($C_1$–$C_6$ alkyl)sulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a $C_1$–$C_6$ tri($C_1$–$C_6$ alkyl) silanealkyl radical; a $C_1$–$C_6$ sulphonamidoalkyl radical; a $C_1$–$C_6$($C_1$–$C_6$ alkyl)carboxyalkyl radical; a $C_1$–$C_6$($C_1$–$C_6$ alkyl)sulphinylalkyl radical; a $C_1$–$C_6$ ($C_1$–$C_6$ alkyl)sulphonylalkyl radical; a $C_1$–$C_6$ ($C_1$–$C_6$ alkyl)ketoalkyl radical; a $C_1$–$C_6$ N-($C_1$–$C_6$ alkyl) carbamylalkyl radical; and a $C_1$–$C_6$ N-($C_1$–$C_6$ alkyl) sulphonamidoalkyl radical;

a and y are integers equal to 0 or 1; with the following conditions:

in the unsaturated cationic groups of formula (II):
when a=0, the linker D is attached to the nitrogen atom,
when a=1, the linker D is attached to one of the ring members E, G, J or L,
y can adopt the value 1 only
1) when the ring members E, G, J and L are simultaneously a carbon atom and when the radical $R_7$ is carried by the nitrogen atom of the unsaturated ring; or
2) when at least one of the ring members E, G, J and L is chosen from a nitrogen atom to which the radical $R_7$ is attached;

in the unsaturated cationic groups of formula (III):
when a=0, the linker D is attached to the nitrogen atom, when a=1, the linker D is attached to one of the ring members E, G, J, L or M, y can adopt the value 1 only
1) when at least one of the ring members E, G, J, L and M is chosen from a divalent atom and
2) when the radical $R_7$ is carried by the nitrogen atom of the unsaturated ring;

in the saturated cationic groups of formula (IV):
when a=0, then the linker D is attached to the nitrogen atom which carries the radicals $R_8$ to $R_{10}$,
when a=1, then two of the radicals $R_8$ to $R_{10}$, together with the nitrogen atom to which they are attached, form a ring chosen from 5- and 6-membered saturated rings, and the linker D is carried by a carbon atom of the said ring;

$X^-$ is chosen from monovalent and divalent anions;

with the proviso that at least one of $R_1$, $R_2$ and $R_3$ is a group Z.

2. At least one chemical according to claim 1, wherein in said formulas (II), (III), and (IV), D is chosen from linear and branched alkyl chains having from 1 to 14 carbon atoms.

3. At least one chemical according to claim 2, wherein said alkyl chains are interrupted by at least one heteroatom chosen from oxygen, sulphur, and nitrogen atoms.

4. At least one chemical according to claim 1, wherein the rings of the unsaturated group Z of formula (II) are chosen from pyrrole, imidazole, pyrazole, oxazole, thiazole and triazole rings.

5. At least one chemical according to claim 1, wherein the rings of the unsaturated group Z of formula (III) are chosen from pyridine, pyrimidine, pyrazine, oxazine and triazine rings.

6. At least one chemical according to claim 1, wherein two of the radicals $R_8$, $R_9$ and $R_{10}$ in said saturated group Z of formula (IV) form a ring chosen from a pyrrolidine ring, a piperidine ring, a piperazine ring and a morpholine ring.

7. At least one chemical according to claim 1, wherein $X^-$ is chosen from a halogen atom, a hydroxide, a hydrogen sulphate and a $C_1$–$C_6$ alkyl sulphate.

8. At least one chemical according to claim 1 chosen from:
3-[3-(3-amino-5-methylpyrazolo[1,5-a]pyrimidin-7-ylamino)propyl]-1-(2-hydroxyethyl)-3H-imidazol-1-ium chloride,
3-[(3-aminopyrazolo[1,5-a]pyrimidin-7-ylcarbamoyl)methyl]-1-methyl-3H-imidazol-1-ium chloride,
3-(3-amino-7-hydroxy-5-methylpyrazolo[1,5-a]pyrimidin-6-ylmethyl)-1-methylpyridinium methyl sulphate,
3-(3-amino-7-hydroxy-5-methylpyrazolo[1,5-a]pyrimidin-6-ylmethyl)-1-(2-hydroxyethyl)pyridinium chloride,
2-[(3-aminopyrazolo[1,5-a]pyrimidin-7-ylamino)methyl]-1,3-dimethyl-3H-imidazol-1-ium methyl sulphate,
3-[(3-aminopyrazolo[1,5-a]pyrimidin-7-ylamino)methyl]-1-methylpyridinium methyl sulphate,
3-[(3-aminopyrazolo[1,5-a]pyrimidin-7-ylamino)methyl]-1-methylpyridinium methyl sulphate,
2-(3,7-diamino-5-methylpyrazolo[1,5-a]pyrimidin-6-ylmethyl)-1,3-dimethyl3H-imidazol-1-ium methyl sulphate,
2-(3-amino-7-hydroxy-5-methylpyrazolo[1,5-a]pyrimidin-6-ylmethyl)-1,3-dimethyl-3H-imidazol-1-ium methyl sulphate,
2-(3,7-diaminopyrazolo[1,5-a]pyrimidin-2-yl)-1-methylpyridinium methyl sulphate,
[3-(3-amino-5-methlpyrazolo[1,5-a]pyrimidin-7-ylamino)propyl]trimethylammonium chloride,
[3-(3-amino-5-methylpyrazolo[1,5-a]pyrimidin-7-ylamino)propyl]trimethylammonium methyl sulphate,
1-[3-(3-amino-5-methylpyrazolo[1,5-a]pyrimidin-7-ylamino)propyl]-1-methylpiperidinium chloride,
1-[3-(3-amino-5-methylpyrazolo[1,5-a]pyrimidin-7-ylamino)propyl]-1-methylpiperdinium methyl sulphate,
4-[3-(3-amino-5-methyl pyrazolo[1,5-a]pyrimidin-7-ylamino)propyl]4-methylmorpholin-4-ium chloride,
4-[3-(3-amino-5-methyl pyrazolo[1,5-a]pyrimidin-7-ylamino)propyl]4-methylmorpholin-4-ium methyl sulphate,
and the acid-addition salts thereof.

9. At least one chemical according to claim 8 chosen from:
3-[3-(3-amino-5-methylpyrazolo[1,5-a]pyrimidin-7-ylamino)propyl]-1-(2-hydroxyethyl)-3H-imidazol-1-ium chloride,
3-(3-amino-7-hydroxy-5methyl pyrazolo[1,5-a]pyrimidin-6-ylmethyl)-1-methylpyridinium methyl sulphate,
3-(3-amino-7-hydroxy-5-methylpyrazolo[1,5-a]pyrimidin-6-ylmethyl)-1-(2-hydroxyethyl)pyridinium chloride,
4-[3-(3-amino-5-methyl pyrazolo[1,5-a]pyrimidin-7-ylamino)propyl]-4-methylmorpholin-4-ium chloride,
4-[3-(3-amino-5-methyl pyrazolo[1,5-a]pyrimidin-7-ylamino)propyl]-4-methylmorpholin-4-ium methyl sulphate,
and the acid-addition salts thereof.

10. At least one chemical according to claim 1, wherein said acid-addition salts are chosen from hydrochlorides, hydrobromides, sulphates, citrates, succinates, tartrates, lactates and acetates.

11. At least one chemical according to claim 8, wherein said acid-addition salts are chosen from hydrochlorides, hydrobromides, sulphates, citrates, succinates, tartrates, lactates and acetates.

12. At least one chemical according to claim 9, wherein said acid-addition salts are chosen from hydrochlorides, hydrobromides, sulphates, citrates, succinates, tartrates, lactates and acetates.

13. A composition for the oxidation dyeing of keratinous fibers, comprising, in a medium suitable for dyeing, at least one oxidation base chosen from compounds of formula (I) and acid addition salts thereof:

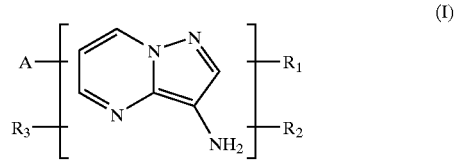

(I)

in which:

$R_1$, $R_2$ and $R_3$, which may be identical or different, are each chosen from a hydrogen atom; a halogen atom; a group Z; a ($C_1$–$C_6$ alkyl)carbonyl radical; an amino ($C_1$–$C_6$ alkyl)carbonyl radical; an N-Z-amino($C_1$–$C_6$ alkyl)carbonyl radical; an N-($C_1$–$C_6$ alkyl)amino ($C_1$–$C_6$ alkyl)carbonyl radical; an N,N-di($C_1$–$C_6$ alkyl)amino($C_1$–$C_6$ alkyl)carbonyl radical; an amino($C_1$–$C_6$ alkyl)carbonyl($C_1$–$C_6$ alkyl) radical; an N-Z-amino($C_1$–$C_6$ alkyl)carbonyl($C_1$–$C_6$ alkyl) radical; an N-($C_1$–$C_6$ alkyl)amino($C_1$–$C_6$ alkyl)carbonyl($C_1$–$C_6$ alkyl) radical; an N,N-di($C_1$–$C_6$ alkyl)amino($C_1$–$C_6$ alkyl)carbonyl($C_1$–$C_6$ alkyl) radical; a carboxyl radical; a ($C_1$–$C_6$ alkyl)carboxyl radical; a ($C_1$–$C_6$ alkyl)sulphonyl radical; an aminosulphonyl radical; an N-Z-aminosulphonyl radical; an N-($C_1$–$C_6$ alkyl)aminosulphonyl radical; an N,N-di($C_1$–$C_6$ alkyl)aminosulphonyl radical; an aminosulphonyl($C_1$–$C_6$ alkyl) radical; an N-Z-aminosulphonyl($C_1$–$C_6$ alkyl) radical; an N-($C_1$–$C_6$ alkyl)aminosulphonyl($C_1$–$C_6$ alkyl) radical; an N,N-di($C_1$–$C_6$ alkyl)aminosulphonyl($C_1$–$C_6$ alkyl) radical; a carbamyl radical; an N-($C_1$–$C_6$ alkyl)carbamyl radical; an N,N-di($C_1$–$C_6$ alkyl)carbamyl radical; a carbamyl($C_1$–$C_6$ alkyl) radical; an N-($C_1$–$C_6$ alkyl)carbamyl($C_1$–$C_6$ alkyl) radical; an N,N-di($C_1$–$C_6$ alkyl)carbamyl($C_1$–$C_6$ alkyl) radical; a $C_1$–$C_6$ alkyl radical; a hydroxyl radical; a nitro radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ trifluoroalkyl radical; a cyano radical; a group $OR_6$; a group $SR_6$; an amino radical; an N-($C_1$–$C_6$ alkyl)amino radical; an N,N-di($C_1$–$C_6$ alkyl)amino radical, wherein the two alkyl substituents may form a ring chosen from 5-and 6-membered rings; an N-hydroxy($C_1$–$C_6$ alkyl)amino radical; an N,N-bis(hydroxy($C_1$–$C_6$ alkyl))amino radical; an N-polyhydroxy($C_2$–$C_6$ alkyl)amino radical; an bis(polyhydroxy($C_2$–$C_6$ alkyl))amino radical; an amino($C_1$–$C_6$ alkyl)amino radical, in which the terminal amino group is unsubstituted or substituted by one or two $C_1$–$C_6$ alkyl radicals, where the alkyl radicals may form a ring chosen from saturated and unsaturated 5- and 6-membered rings; an amino group protected by at least one group chosen from a ($C_1$–$C_6$ alkyl)carbonyl, a trifluoro($C_1$–$C_6$ alkyl)carbonyl, an amino($C_1$–$C_6$ alkyl)carbonyl, an N-Z-amino($C_1$–$C_6$ alkyl)carbonyl, an N-($C_1$–$C_6$ alkyl)amino($C_1$–$C_6$ alkyl)carbonyl, an N,N-di($C_1$–$C_6$ alkyl)amino($C_1$–$C_6$ alkyl)carbonyl radical, an N,N-di($C_1$–$C_6$ alkyl)amino($C_1$–$C_6$ alkyl) formyl radical, and a group Z;

$R_6$ is chosen from a $C_1$–$C_6$ alkyl radical; a $C_1$–$C_6$ monohydroxyalkyl radical; a $C_2$–$C_6$ polyhydroxyalkyl radical; a group Z; a $C_1$–$C_6$ ($C_1$–$C_6$ alkoxy)alkyl radical; an aryl radical; a benzyl radical; a $C_1$–$C_6$ carboxyalkyl radical; a $C_1$–$C_6$ ($C_1$–$C_6$ alkyl)carboxyalkyl radical; a $C_1$–$C_6$ cyanoalkyl radical; a $C_1$–$C_6$ carbamylalkyl radical; a $C_1$–$C_6$ N-($C_1$–$C_6$ alkyl)carbamylalkyl radical; a $C_1$–$C_6$ N,N-di($C_1$–$C_6$ alkyl)carbamylalkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)aminosulphonylalkyl radical; a $C_1$–$C_6$ N,N-di($C_1$–$C_6$ alkyl)aminosulphonylalkyl radical; a $C_1$–$C_6$ ($C_1$–$C_6$ alkyl)sulphinylalkyl radical; a $C_1$–$C_6$ ($C_1$–$C_6$ alkyl)sulphonylalkyl radical; a $C_1$–$C_6$ ($C_1$–$C_6$ alkyl)carbonylalkyl radical; a $C_1$–$C_6$ aminoalkyl radical; a $C_1$–$C_6$ aminoalkyl radical whose amine is substituted by one or two radicals chosen from $C_1$–$C_6$ alkyl, monohydroxy($C_1$–$C_6$ alkyl), polyhydroxy($C_2$–$C_6$ alkyl), ($C_1$–$C_6$ alkyl)carbonyl, formyl, trifluoro($C_1$–$C_6$ alkyl)carbonyl, and ($C_1$–$C_6$ alkyl)sulphonyl radicals, and a group Z;

A is chosen from $-NR_4R_5$ and a hydroxyl radical;

$R_4$ and $R_5$, are independently chosen from a hydrogen atom; a group Z; a $C_1$–$C_6$ alkyl radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; an aryl radical; a benzyl radical; a $C_1$–$C_6$ cyanoalkyl radical; a $C_1$–$C_6$ carbamylalkyl radical; a $C_1$–$C_6$ N-($C_1$–$C_6$ alkyl)carbamylalkyl radical; a $C_1$–$C_6$ N,N-di($C_1$–$C_6$ alkyl)carbamylalkyl radical; a $C_1$–$C_6$ thiocarbamylalkyl radical; a $C_1$–$C_6$ trifluoroalkyl radical; a $C_1$–$C_6$ sulphoalkyl radical; a $C_1$–$C_6$ ($C_1$–$C_6$ alkyl)carboxyalkyl radical; a $C_1$–$C_6$ ($C_1$–$C_6$ alkyl)sulphinylalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkylaminosulphonylalkyl radical; a $C_1$–$C_6$ N,N-di($C_1$–$C_6$ alkyl)aminosulphonylalkyl radical; a $C_1$–$C_6$ ($C_1$–$C_6$ alkyl)carbonylalkyl radical; a $C_1$–$C_6$ aminoalkyl radical; and a $C_1$–$C_6$ aminoalkyl radical whose amine is substituted by one or two radicals chosen from $C_1$–$C_6$ alkyl, $C_1$–$C_6$ monohydroxyalkyl, $C_2$–$C_6$ polyhydroxyalkyl, ($C_1$–$C_6$ alkyl)carbonyl, ($C_1$-alkyl)sulphonyl, formyl, and trifluoro($C_1$–$C_6$ alkyl)carbonyl radicals, and a group Z;

wherein one and only one of the radicals $R_4$ and $R_5$ may also be chosen from a ($C_1$–$C_6$ alkyl)carbonyl radical; a formyl radical; a trifluoro($C_1$–$C_6$ alkyl)carbonyl radical; an amino($C_1$–$C_6$ alkyl)carbonyl radical; an N-Z-amino($C_1$–$C_6$ alkyl)carbonyl radical; an N-($C_1$–$C_6$ alkyl)amino($C_1$–$C_6$ alkyl)carbonyl radical; and an N,N-di($C_1$–$C_6$ alkyl)amino($C_1$–$C_6$ alkyl)carbonyl radical;

Z is chosen from the unsaturated cationic groups of formulae (II) and (III) below and the saturated cationic groups of formula (IV) below:

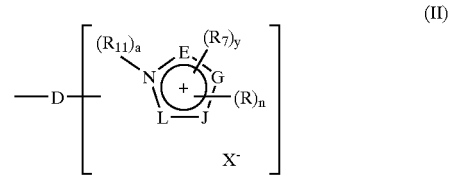

(II)

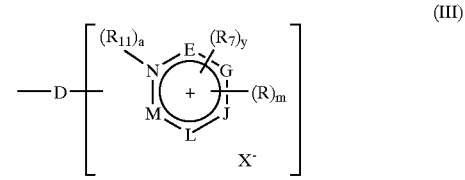

(III)

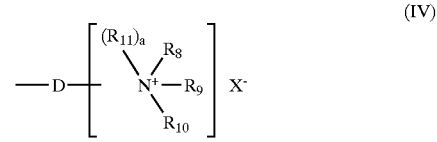

(IV)

in which:

D is a linker which is chosen from linear and branched alkyl chains and may be interrupted by at least one heteroatom atom and may be substituted by at least one of a hydroxyl and a $C_1$–$C_6$ alkoxy radical, and may carry at least one ketone function;

the ring members E, G, J, L and M, which are identical or different, are chosen from carbon, oxygen, sulphur and nitrogen atoms;

n is an integer ranging from 0 to 4;

m is an integer ranging from 0 to 5;

the radicals R, which are identical or different, may be chosen from a group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a $C_1$–$C_6$ tri($C_1$–$C_6$ alkyl)silanealkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$ alkyl)thio radical; an amino radical; an amino radical protected by a group chosen from ($C_1$–$C_6$ alkyl)carbonyl, carbamyl, and ($C_1$–$C_6$ alkyl)sulphonyl; and groups NHR" and NR"R'" in which R" and R''', which are identical or different, are chosen from a $C_1$–$C_6$ alkyl radical, a $C_1$–$C_6$ monohydroxyalkyl radical and a $C_2$–$C_6$ polyhydroxyalkyl radical;

$R_7$ is chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ cyanoalkyl radical; a $C_1$–$C_6$ tri($C_1$–$C_6$ alkyl)silanealkyl radical; a $C_1$–$C_6$ ($C_1$–$C_6$ alkoxy)alkyl radical; a carbamyl($C_1$–$C_6$ alkyl) radical; a $C_1$–$C_6$ ($C_1$–$C_6$ alkyl)carboxyalkyl radical; a benzyl radical; and a group Z;

$R_8$, $R_9$ and $R_{10}$, which are identical or different, are chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ cyanoalkyl radical; an aryl radical; a benzyl radical; a $C_1$–$C_6$ amidoalkyl radical; a $C_1$–$C_6$ tri($C_1$–$C_6$ alkyl)silanealkyl radical; and a $C_1$–$C_6$ aminoalkyl radical whose amine is protected by at least one of a ($C_1$–$C_6$ alkyl)carbonyl, amido, carboxyl and ($C_1$–$C_6$ alkyl)sulphonyl radical;

two of the radicals $R_8$, $R_9$ and $R_{10}$ may form, together with the nitrogen to which they are attached, a ring chosen from saturated 5- and 6-membered carbon-containing rings which may contain at least one heteroatom, wherein said rings may contain a substituent chosen from a halogen atom; a hydroxyl radical; a $C_1$–$C_6$ alkyl radical, a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a $C_1$–$C_6$ tri($C_1$–$C_6$ alkyl)silanealkyl radical; an amido radical; an aldehydo radical; a carboxyl radical; a $C_1$–$C_6$ ketoalkyl radical; a thio radical; a $C_1$–$C_6$ thioalkyl radical; a ($C_1$–$C_6$ alkyl)thio radical; an amino radical; and an amino radical protected by a group chosen from ($C_1$–$C_6$ alkyl)carbonyl; carbamyl and ($C_1$–$C_6$ alkyl)sulphonyl radical;

one of the radicals $R_8$, $R_9$ and $R_{10}$ may be chosen from a second group Z, identical to or different from the first group Z;

$R_{11}$ may be chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is protected by at least one of a ($C_1$–$C_6$ alkyl)carbonyl, a carbamyl, and a ($C_1$–$C_6$ alkyl)sulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a $C_1$–$C_6$ tri($C_1$–$C_6$ alkyl)silanealkyl radical; a $C_1$–$C_6$ sulphonamidoalkyl radical; a $C_1$–$C_6$ ($C_1$–$C_6$ alkyl)carboxyalkyl radical; a $C_1$–$C_6$ ($C_1$–$C_6$ alkyl)sulphinylalkyl radical; a $C_1$–$C_6$ ($C_1$–$C_6$ alkyl)sulphonylalkyl radical; a $C_1$–$C_6$ ($C_1$–$C_6$ alkyl)ketoalkyl radical; a $C_1$–$C_6$ N-($C_1$–$C_6$ alkyl) carbamylalkyl radical; and a $C_1$–$C_6$ N-($C_1$–$C_6$ alkyl) sulphonamidoalkyl radical;

a and y are integers equal to 0 or 1; with the following conditions:
in the unsaturated cationic groups of formula (II):
when a=0, the linker D is attached to the nitrogen atom,
when a=1, the linker D is attached to one of the ring members E, G, J or L,
y can adopt the value 1 only
1) when the ring members E, G, J and L are simultaneously a carbon atom and when the radical $R_7$ is carried by the nitrogen atom of the unsaturated ring; or
2) when at least one of the ring members E, G, J and L is chosen from a nitrogen atom to which the radical $R_7$ is attached;
in the unsaturated cationic groups of formula (III):
when a=0, the linker D is attached to the nitrogen atom,
when a=1, the linker D is attached to one of the ring members E, G, J, L or M,
y can adopt the value 1 only
1) when at least one of the ring members E, G, J, L and M is chosen from a divalent atom and
2) when the radical $R_7$ is carried by the nitrogen atom of the unsaturated ring;
in the saturated cationic groups of formula (IV):
when a=0, then the linker D is attached to the nitrogen atom which carries the radicals $R_8$ to $R_{10}$,
when a=1, then two of the radicals $R_8$ to $R_{10}$, together with the nitrogen atom to which they are attached, form a ring chosen from 5- and 6-membered saturated rings, and the linker D is carried by a carbon atom of the said ring;

$X^-$ is chosen from monovalent and divalent anions;
with the proviso that at least one of $R_1$, $R_2$ and $R_3$ is a group Z.

14. A composition according to claim 13, wherein in said formulas (II), (III), and (IV), D is chosen from linear and branched alkyl chains having from 1 to 14 carbon atoms.

15. A composition according to claim 13, wherein said alkyl chains are interrupted by at least one heteroatom chosen from oxygen, sulphur, and nitrogen atoms.

16. A composition according to claim 13, wherein the rings of the unsaturated group Z of formula (II) are chosen from pyrrole, imidazole, pyrazole, oxazole, thiazole and triazole rings.

17. A composition according to claim 13, wherein the rings of the unsaturated group Z of formula (III) are chosen from pyridine, pyrimidine, pyrazine, oxazine and triazine rings.

18. A composition according to claim 13, wherein two of the radicals $R_8$, $R_9$ and $R_{10}$ in said saturated group Z of formula (IV) form a ring chosen from a pyrrolidine ring, a piperidine ring, a piperazine ring and a morpholine ring.

19. A composition according to claim 13, wherein $X^-$ is chosen from a halogen atom, a hydroxide, a hydrogen sulphate and a $C_1$–$C_6$ alkyl sulphate.

20. A composition according to claim 13, wherein said at least one compound of formula (I) is present in said composition in an amount ranging from 0.0005 to 12% by weight relative to the total weight of the composition.

21. A composition according to claim 20, wherein said at least one compound of formula (I) is present in said composition in an amount ranging from 0.005 to 6% by weight relative to the total weight of the dyeing composition.

22. A composition according to claim 13, further comprising at least one additional oxidation base chosen from para-phenylenediamines, bisphenylalkylenediamines, para-aminophenols, ortho-aminophenols and heterocyclic bases other than the compounds of formula (I).

23. A composition according to claim 22, wherein the at least one additional oxidation base is present in said composition in an amount ranging from 0.0005 to 12% by weight relative to the total weight of the dyeing composition.

24. A composition according to claim 13, further comprising at least one of couplers and direct dyes.

25. A composition according to claim 24, wherein said couplers are chosen from meta-phenylenediamines, meta-aminophenols and metadiphenols and heterocyclic couplers, and the acid-addition salts thereof.

26. A composition according to claim 25, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and the acid-addition salts thereof.

27. A composition according to claim 24, wherein at least one coupler is present in said composition in an amount ranging from 0.0001 to 10% by weight relative to the total weight of the composition.

28. A composition according to claim 25, wherein the acid-addition salts are chosen from the hydrochlorides, hydrobromides, sulphates, citrates, succinates, tartrates, lactates and acetates.

29. A composition according to claim 26, wherein the acid-addition salts are chosen from the hydrochlorides, hydrobromides, sulphates, citrates, succinates, tartrates, lactates and acetates.

30. A method for dyeing keratinous fibers comprising
applying a dyeing composition to said keratinous fibers, and
developing color with the aid of at least one oxidizing agent,
wherein said at least one oxidizing agent is added to the dyeing composition at the time of application or which is present in an oxidizing composition which is applied simultaneously with said dyeing composition, either sequentially or separately,
wherein said dyeing composition comprises, in a medium suitable for dyeing,
at least one oxidation base chosen from compounds of formula (I) and acid addition salts thereof:

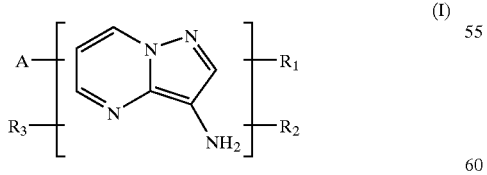

(I)

in which:
$R_1$, $R_2$ and $R_3$, which may be identical or different, are each chosen from a hydrogen atom; a halogen atom; a group Z; a ($C_1$–$C_6$ alkyl)carbonyl radical; an amino ($C_1$–$C_6$ alkyl)carbonyl radical; an N-Z-amino($C_1$–$C_6$ alkyl)carbonyl radical; an N-($C_1$–$C_6$ alkyl)amino ($C_1$–$C_6$ alkyl)carbonyl radical; an N,N-di($C_1$–$C_6$ alkyl) amino($C_1$–$C_6$ alkyl)carbonyl radical; an amino($C_1$–$C_6$ alkyl)carbonyl($C_1$–$C_6$ alkyl) radical; an N-Z-amino ($C_1$–$C_6$ alkyl)carbonyl($C_1$–$C_6$ alkyl) radical; an N-($C_1$–$C_6$ alkyl)amino($C_1$–$C_6$ alkyl)carbonyl($C_1$–$C_6$ alkyl) radical; an N,N-di($C_1$–$C_6$ alkyl)amino($C_1$–$C_6$ alkyl)carbonyl($C_1$–$C_6$ alkyl) radical; a carboxyl radical; a ($C_1$–$C_6$ alkyl)carboxyl radical; a ($C_1$–$C_6$ alkyl) sulphonyl radical; an aminosulphonyl radical; an N-Z-aminosulphonyl radical; an N-($C_1$–$C_6$ alkyl) aminosulphonyl radical; an N,N-di($C_1$–$C_6$ alkyl) aminosulphonyl radical; an aminosulphonyl($C_1$–$C_6$ alkyl) radical; an N-Z-aminosulphonyl($C_1$–$C_6$ alkyl) radical; an N-($C_1$–$C_6$ alkyl)aminosulphonyl($C_1$–$C_6$ alkyl) radical; an N,N-di($C_1$–$C_6$ alkyl)aminosulphonyl ($C_1$–$C_6$ alkyl) radical; a carbamyl radical; an N-($C_1$–$C_6$ alkyl)carbamyl radical; an N,N-di($C_1$–$C_6$ alkyl) carbamyl radical; a carbamyl($C_1$–$C_6$ alkyl) radical; an N-($C_1$–$C_6$ alkyl)carbamyl($C_1$–$C_6$ alkyl) radical; an N,N-di($C_1$–$C_6$ alkyl)carbamyl($C_1$–$C_6$ alkyl) radical; a $C_1$–$C_6$ alkyl radical; a hydroxyl radical; a nitro radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ trifluoroalkyl radical; a cyano radical; a group $OR_6$; a group $SR_6$; an amino radical; an N-($C_1$–$C_6$ alkyl)amino radical; an N,N-di($C_1$–$C_6$ alkyl) amino radical, wherein the two alkyl substituents may form a ring chosen from 5- and 6-membered rings; an N-hydroxy($C_1$–$C_6$ alkyl)amino radical; an N,N-bis (hydroxy($C_1$–$C_6$ alkyl))amino radical; an N-polyhydroxy($C_2$–$C_6$ alkyl)amino radical; an N,N-bis (polyhydroxy($C_2$–$C_6$ alkyl))amino radical; an amino ($C_1$–$C_6$ alkyl)amino radical, in which the terminal amino group is unsubstituted or substituted by one or two $C_1$–$C_6$ alkyl radicals, where the alkyl radicals may form a ring chosen from saturated and unsaturated 5- and 6-membered rings; an amino group protected by at least one group chosen from a ($C_1$–$C_6$ alkyl)carbonyl, a trifluoro($C_1$–$C_6$ alkyl)carbonyl, an amino($C_1$–$C_6$ alkyl)carbonyl, an N-Z-amino($C_1$–$C_6$ alkyl)carbonyl, an N-($C_1$–$C_6$ alkyl)amino($C_1$–$C_6$ alkyl)carbonyl, an N,N-di($C_1$–$C_6$ alkyl)amino($C_1$–$C_6$ alkyl)carbonyl radical, an N,N-di($C_1$–$C_6$ alkyl)amino($C_1$–$C_6$ alkyl) formyl radical, and a group Z;

$R_6$ is chosen from a $C_1$–$C_6$ alkyl radical; a $C_1$–$C_6$ monohydroxyalkyl radical; a $C_2$–$C_6$ polyhydroxyalkyl radical; a group Z; a $C_1$–$C_6$ ($C_1$–$C_6$ alkoxy)alkyl radical; an aryl radical; a benzyl radical; a $C_1$–$C_6$ carboxyalkyl radical; a $C_1$–$C_6$ ($C_1$–$C_6$ alkyl)carboxyalkyl radical; a $C_1$–$C_6$ cyanoalkyl radical; a $C_1$–$C_6$ carbamylalkyl radical; a $C_1$–$C_6$ N-($C_1$–$C_6$ alkyl)carbamylalkyl radical; a $C_1$–$C_6$ N,N-di($C_1$–$C_6$ alkyl)carbamylalkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)aminosulphonylalkyl radical; a $C_1$–$C_6$ N,N-di($C_1$–$C_6$ alkyl) aminosulphonylalkyl radical; a $C_1$–$C_6$ ($C_1$–$C_6$ alkyl) sulphinylalkyl radical; a $C_1$–$C_6$ ($C_1$–$C_6$ alkyl) sulphonylalkyl radical; a $C_1$–$C_6$ ($C_1$–$C_6$ alkyl) carbonylalkyl radical; a $C_1$–$C_6$ aminoalkyl radical; a $C_1$–$C_6$ aminoalkyl radical whose amine is substituted by one or two radicals chosen from $C_1$–$C_6$ alkyl, monohydroxy($C_1$–$C_6$ alkyl), polyhydroxy($C_2$–$C_6$ alkyl), ($C_1$–$C_6$ alkyl)carbonyl, formyl, trifluoro($C_1$–$C_6$ alkyl)carbonyl, and ($C_1$–$C_6$ alkyl)sulphonyl radicals, and a group Z;

A is chosen from —$NR_4R_5$ and a hydroxyl radical;

$R_4$ and $R_5$, are independently chosen from a hydrogen atom; a group Z; a $C_1$–$C_6$ alkyl radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; an aryl radical; a benzyl radical; a $C_1$–$C_6$ cyanoalkyl radical; a $C_1$–$C_6$ carbamylalkyl radical; a $C_1$–$C_6$ N-($C_1$–$C_6$ alkyl) carbamylalkyl radical; a $C_1$–$C_6$ N,N-di($C_1$–$C_6$ alkyl) carbamylalkyl radical; a $C_1$–$C_6$ thiocarbamylalkyl radical; a $C_1$–$C_6$ trifluoroalkyl radical; a $C_1$–$C_6$ sulphoalkyl radical; a $C_1$–$C_6$ ($C_1$–$C_6$ alkyl)carboxyalkyl radical; a $C_1$–$C_6$ ($C_1$–$C_6$ alkyl)sulphinylalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)-aminosulphonylalkyl radical; a $C_1$–$C_6$ N,N-di($C_1$–$C_6$ alkyl)aminosulphonylalkyl radical; a $C_1$–$C_6$ ($C_1$–$C_6$ alkyl)carbonylalkyl radical; a $C_1$–$C_6$ aminoalkyl radical; and a $C_1$–$C_6$ aminoalkyl radical whose amine is substituted by one or two radicals chosen from $C_1$–$C_6$ alkyl, $C_1$–$C_6$ monohydroxyalkyl, $C_2$–$C_6$ polyhydroxyalkyl, ($C_1$–$C_6$ alkyl)carbonyl, ($C_1$-alkyl)sulphonyl, formyl, and trifluoro($C_1$–$C_6$ alkyl)carbonyl radicals, and a group Z;

wherein one and only one of the radicals $R_4$ and $R_5$ may also be chosen from a ($C_1$–$C_6$ alkyl)carbonyl radical; a formyl radical; a trifluoro($C_1$–$C_6$ alkyl)carbonyl radical; an amino($C_1$–$C_6$ alkyl)carbonyl radical; an N-Z-amino($C_1$–$C_6$ alkyl)carbonyl radical; an N-($C_1$–$C_6$ alkyl)amino($C_1$–$C_6$ alkyl)carbonyl radical; and an N,N-di($C_1$–$C_6$ alkyl)amino($C_1$–$C_6$ alkyl)carbonyl radical;

Z is chosen from the unsaturated cationic groups of formulae (II) and (III) below and the saturated cationic groups of formula (IV) below:

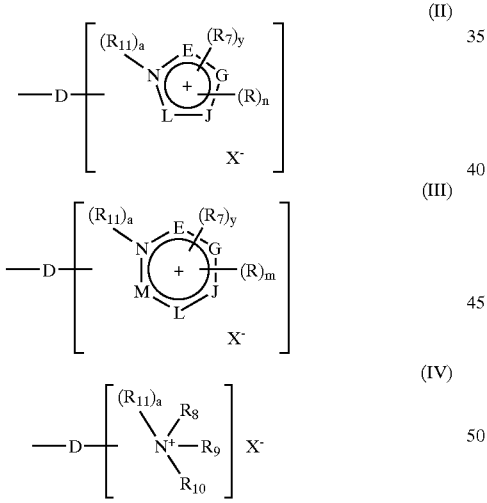

in which:

D is a linker which is chosen from linear and branched alkyl chains and may be interrupted by at least one heteroatom atom and may be substituted by at least one of a hydroxyl and a $C_1$–$C_6$ alkoxy radical, and may carry at least one ketone function;

the ring members E, G, J, L and M, which are identical or different, are chosen from carbon, oxygen, sulphur and nitrogen atoms;

n is an integer ranging from 0 to 4;

m is an integer ranging from 0 to 5;

the radicals R, which are identical or different, may be chosen from a group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a $C_1$–$C_6$ tri($C_1$–$C_6$ alkyl) silanealkyl radical; an amido radical; an aldehydo radical; a carboxyl radical; a $C_1$–$C_6$ alkylcarbonyl radical; a thio radical; a $C_1$–$C_6$ thioalkyl radical; a ($C_1$–$C_6$ alkyl)thio radical; an amino radical; an amino radical protected by a group chosen from ($C_1$–$C_6$ alkyl) carbonyl, carbamyl, and ($C_1$–$C_6$ alkyl)sulphonyl; and groups NHR" and NR"R'" in which R" and R'", which are identical or different, are chosen from a $C_1$–$C_6$ alkyl radical, a $C_1$–$C_6$ monohydroxyalkyl radical and a $C_2$–$C_6$ polyhydroxyalkyl radical;

$R_7$ is chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ cyanoalkyl radical; a $C_1$–$C_6$ tri($C_1$–$C_6$ alkyl)silanealkyl radical; a $C_1$–$C_6$ ($C_1$–$C_6$ alkoxy)alkyl radical; a carbamyl($C_1$–$C_6$ alkyl) radical; a $C_1$–$C_6$ ($C_1$–$C_6$ alkyl)carboxyalkyl radical; a benzyl radical; and a group Z;

$R_8$, $R_9$ and $R_{10}$, which are identical or different, are chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ cyanoalkyl radical; an aryl radical; a benzyl radical; a $C_1$–$C_6$ amidoalkyl radical; a $C_1$–$C_6$ tri($C_1$–$C_6$ alkyl) silanealkyl radical; and a $C_1$–$C_6$ aminoalkyl radical whose amine is protected by at least one of a ($C_1$–$C_6$ alkyl)carbonyl, amido, carboxyl and ($C_1$–$C_6$ alkyl) sulphonyl radical;

two of the radicals $R_8$, $R_9$ and $R_{10}$ may form, together with the nitrogen to which they are attached, a ring chosen from saturated 5- and 6-membered carbon-containing rings which may contain at least one heteroatom, wherein said rings may contain a substituent chosen from a halogen atom; a hydroxyl radical; a $C_1$–$C_6$ alkyl radical, a $C_1$–$C_6$ monohydroxyalkyl radical; a $C_2$–$C_6$ polyhydroxyalkyl radical; a nitro radical; a cyano radical; a $C_1$–$C_6$ cyanoalkyl radical; a $C_1$–$C_6$ alkoxy radical; a $C_1$–$C_6$ tri($C_1$–$C_6$ alkyl)silanealkyl radical; an amido radical; an aldehydo radical; a carboxyl radical; a $C_1$–$C_6$ ketoalkyl radical; a thio radical; a $C_1$–$C_6$ thioalkyl radical; a ($C_1$–$C_6$ alkyl)thio radical; an amino radical; and an amino radical protected by a group chosen from ($C_1$–$C_6$ alkyl)carbonyl; carbamyl and ($C_1$–$C_6$ alkyl)sulphonyl radical;

one of the radicals $R_8$, $R_9$ and $R_{10}$ may be chosen from a second group Z, identical to or different from the first group Z;

$R_{11}$ may be chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is protected by at least one of a ($C_1$–$C_6$ alkyl) carbonyl, a carbamyl, and a ($C_1$–$C_6$ alkyl)sulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a $C_1$–$C_6$ tri($C_1$–$C_6$ alkyl) silanealkyl radical; a $C_1$–$C_6$ sulphonamidoalkyl radical; a $C_1$–$C_6$ ($C_1$–$C_6$ alkyl)carboxyalkyl radical; a $C_1$–$C_6$ ($C_1$–$C_6$ alkyl)sulphinylalkyl radical; a $C_1$–$C_6$ ($C_1$–$C_6$ alkyl)sulphonylalkyl radical; a $C_1$–$C_6$ ($C_1$–$C_6$ alkyl)ketoalkyl radical; a $C_1$–$C_6$ N-($C_1$–$C_6$ alkyl) carbamylalkyl radical; and a $C_1$–$C_6$ N-($C_1$–$C_6$ alkyl) sulphonamidoalkyl radical;

a and y are integers equal to 0 or 1; with the following conditions:
in the unsaturated cationic groups of formula (II):
when a=0, the linker D is attached to the nitrogen atom,
when a=1, the linker D is attached to one of the ring members E, G, J or L,
y can adopt the value 1 only
1) when the ring members E, G, J and L are simultaneously a carbon atom and when the radical $R_7$ is carried by the nitrogen atom of the unsaturated ring; or
2) when at least one of the ring members E, G, J and L is chosen from a nitrogen atom to which the radical $R_7$ is attached;
in the unsaturated cationic groups of formula (III):
when a=0, the linker D is attached to the nitrogen atom,
when a=1, the linker D is attached to one of the ring members E, G, J, L or M,
y can adopt the value 1 only
1) when at least one of the ring members E, G, J, L and M is chosen from a divalent atom and
2) when the radical $R_7$ is carried by the nitrogen atom of the unsaturated ring;
in the saturated cationic groups of formula (IV):
when a=0, then the linker D is attached to the nitrogen atom which carries the radicals $R_8$ to $R_{10}$,
when a=1, then two of the radicals $R_8$ to $R_{10}$, together with the nitrogen atom to which they are attached, form a ring chosen from 5- and 6-membered saturated rings, and the linker D is carried by a carbon atom of the said ring;
$X^-$ is chosen from monovalent and divalent anions;
with the proviso that at least one of $R_1$, $R_2$ and $R_3$ is a group Z.

31. The method according to claim 30, wherein the at least one oxidizing agent is chosen from hydrogen peroxide, urea peroxide, alkali metal bromates, persalts and enzymes.

32. The method of claim 30, wherein said keratinous fibers are hair.

33. A multi-compartment dyeing kit comprising at least two compartments, wherein a first compartment contains a dyeing composition and a second compartment contains an oxidizing composition,
wherein said dyeing composition comprises, in a medium suitable for dyeing, at least one oxidation base chosen from compounds of formula (I) and acid addition salts thereof:

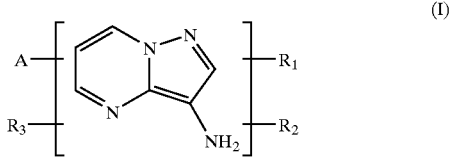

(I)

in which:
$R_1$, $R_2$ and $R_3$, which may be identical or different, are each chosen from a hydrogen atom; a halogen atom; a group Z; a ($C_1$–$C_6$ alkyl)carbonyl radical; an amino($C_1$–$C_6$ alkyl)carbonyl radical; an N-Z-amino($C_1$–$C_6$ alkyl)carbonyl radical; an N-($C_1$–$C_6$ alkyl)amino($C_1$–$C_6$ alkyl)carbonyl radical; an N,N-di($C_1$–$C_6$ alkyl)amino($C_1$–$C_6$ alkyl)carbonyl radical; an amino($C_1$–$C_6$ alkyl)carbonyl($C_1$–$C_6$ alkyl) radical; an N-Z-amino ($C_1$–$C_6$ alkyl)carbonyl($C_1$–$C_6$ alkyl) radical; an N-($C_1$–$C_6$ alkyl)amino($C_1$–$C_6$ alkyl)carbonyl($C_1$–$C_6$ alkyl) radical; an N,N-di($C_1$–$C_6$ alkyl)amino($C_1$–$C_6$ alkyl)carbonyl($C_1$–$C_6$ alkyl) radical; a carboxyl radical; a ($C_1$–$C_6$ alkyl)carboxyl radical; a ($C_1$–$C_6$ alkyl)sulphonyl radical; an aminosulphonyl radical; an N-Z-aminosulphonyl radical; an N-($C_1$–$C_6$ alkyl)aminosulphonyl radical; an N,N-di($C_1$–$C_6$ alkyl)aminosulphonyl radical; an aminosulphonyl($C_1$–$C_6$ alkyl) radical; an N-Z-aminosulphonyl($C_1$–$C_6$ alkyl) radical; an N-($C_1$–$C_6$ alkyl)aminosulphonyl($C_1$–$C_6$ alkyl) radical; an N,N-di($C_1$–$C_6$ alkyl)aminosulphonyl ($C_1$–$C_6$ alkyl) radical; a carbamyl radical; an N-($C_1$–$C_6$ alkyl)carbamyl radical; an N,N-di($C_1$–$C_6$ alkyl)carbamyl radical; a carbamyl($C_1$–$C_6$ alkyl) radical; an N-($C_1$–$C_6$ alkyl)carbamyl($C_1$–$C_6$ alkyl) radical; an N,N-di($C_1$–$C_6$ alkyl)carbamyl($C_1$–$C_6$ alkyl) radical; a $C_1$–$C_6$ alkyl radical; a hydroxyl radical; a nitro radical; a $C_1$–$C_6$ monohydroxyalkyl radical; a $C_2$–$C_6$ polyhydroxyalkyl radical; a $C_1$–$C_6$ ($C_1$–$C_6$ alkoxy)alkyl radical; a $C_1$–$C_6$ trifluoroalkyl radical; a cyano radical; a group $OR_6$; a group $SR_6$; an amino radical; an N-($C_1$–$C_6$ alkyl)amino radical; an N,N-di($C_1$–$C_6$ alkyl)amino radical, wherein the two alkyl substituents may form a ring chosen from 5- and 6-membered rings; an N-hydroxy($C_1$–$C_6$ alkyl)amino radical; an N,N-bis(hydroxy($C_1$–$C_6$ alkyl))amino radical; an N-polyhydroxy($C_2$–$C_6$ alkyl)amino radical; an N,N-bis(polyhydroxy($C_2$–$C_6$ alkyl))amino radical; an amino ($C_1$–$C_6$ alkyl)amino radical, in which the terminal amino group is unsubstituted or substituted by one or two $C_1$–$C_6$ alkyl radicals, where the alkyl radicals may form a ring chosen from saturated and unsaturated 5- and 6-membered rings; an amino group protected by at least one group chosen from a ($C_1$–$C_6$ alkyl)carbonyl, a trifluoro($C_1$–$C_6$ alkyl)carbonyl, an amino($C_1$–$C_6$ alkyl)carbonyl, an N-Z-amino($C_1$–$C_6$ alkyl)carbonyl, an N-($C_1$–$C_6$ alkyl)amino($C_1$–$C_6$ alkyl)carbonyl, an N,N-di($C_1$–$C_6$ alkyl)amino($C_1$–$C_6$ alkyl)carbonyl radical, an N,N-di($C_1$–$C_6$ alkyl)amino($C_1$–$C_6$ alkyl) formyl radical, and a group Z;

$R_6$ is chosen from a $C_1$–$C_6$ alkyl radical; a $C_1$–$C_6$ monohydroxyalkyl radical; a $C_2$–$C_6$ polyhydroxyalkyl radical; a group Z; a $C_1$–$C_6$ ($C_1$–$C_6$ alkoxy)alkyl radical; an aryl radical; a benzyl radical; a $C_1$–$C_6$ carboxyalkyl radical; a $C_1$–$C_6$ ($C_1$–$C_6$ alkyl)carboxyalkyl radical; a $C_1$–$C_6$ cyanoalkyl radical; a $C_1$–$C_6$ carbamylalkyl radical; a $C_1$–$C_6$ N-($C_1$–$C_6$ alkyl)carbamylalkyl radical; a $C_1$–$C_6$ N,N-di($C_1$–$C_6$ alkyl)carbamylalkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; a $C_1$–$C_6$ N-($C_1$–$C_6$ alkyl)aminosulphonylalkyl radical; a $C_1$–$C_6$ N,N-di($C_1$–$C_6$ alkyl)aminosulphonylalkyl radical; a $C_1$–$C_6$ ($C_1$–$C_6$ alkyl)sulphinylalkyl radical; a $C_1$–$C_6$ ($C_1$–$C_6$ alkyl)sulphonylalkyl radical; a $C_1$–$C_6$ ($C_1$–$C_6$ alkyl)carbonylalkyl radical; a $C_1$–$C_6$ aminoalkyl radical; a $C_1$–$C_6$ aminoalkyl radical whose amine is substituted by one or two radicals chosen from $C_1$–$C_6$ alkyl, monohydroxy($C_1$–$C_6$ alkyl), polyhydroxy($C_2$–$C_6$ alkyl), ($C_1$–$C_6$ alkyl)carbonyl, formyl, trifluoro($C_1$–$C_6$ alkyl)carbonyl, and ($C_1$–$C_6$ alkyl)sulphonyl radicals, and a group Z;

A is chosen from —$NR_4R_5$ and a hydroxyl radical;

$R_4$ and $R_5$, are independently chosen from a hydrogen atom; a group Z; a $C_1$–$C_6$ alkyl radical; a $C_1$–$C_6$ monohydroxyalkyl radical; a $C_2$–$C_6$ polyhydroxyalkyl radical; a C$_1$–C$_6$ (C$_1$–C$_6$ alkoxy)alkyl radical; an aryl radical; a benzyl radical; a C$_1$–C$_6$ cyanoalkyl radical; a C$_1$–C$_6$ carbamylalkyl radical; a C$_1$–C$_6$ N-(C$_1$–C$_6$ alkyl) carbamylalkyl radical; a C$_1$–C$_6$ N,N-di(C$_1$–C$_6$ alkyl) carbamylalkyl radical; a C$_1$–C$_6$ thiocarbamylalkyl radical; a C$_1$–C$_6$ trifluoroalkyl radical; a C$_1$–C$_6$ sulphoalkyl radical; a C$_1$–C$_6$ (C$_1$–C$_6$ alkyl)carboxyalkyl radical; a C$_1$–C$_6$ (C$_1$–C$_6$ alkyl)sulphinylalkyl radical; a C$_1$–C$_6$ aminosulphonylalkyl radical; a C$_1$–C$_6$ N-Z-aminosulphonylalkyl radical; a C$_1$–C$_6$ N-(C$_1$–C$_6$ alkyl)-aminosulphonylalkyl radical; a C$_1$–C$_6$ N,N-di(C$_1$–C$_6$ alkyl)aminosulphonylalkyl radical; a C$_1$–C$_6$ (C$_1$–C$_6$ alkyl)carbonylalkyl radical; a C$_1$–C$_6$ aminoalkyl radical; and a C$_1$–C$_6$ aminoalkyl radical whose amine is substituted by one or two radicals chosen from C$_1$–C$_6$ alkyl, C$_1$–C$_6$ monohydroxyalkyl, C$_2$–C$_6$ polyhydroxyalkyl, (C$_1$–C$_6$ alkyl)carbonyl, (C$_1$-alkyl) sulphonyl, formyl, and trifluoro(C$_1$–C$_6$ alkyl)carbonyl radicals, and a group Z;

wherein one and only one of the radicals R$_4$ and R$_5$ may also be chosen from a (C$_1$–C$_6$ alkyl)carbonyl radical; a formyl radical; a trifluoro(C$_1$–C$_6$ alkyl)carbonyl radical; an amino(C$_1$–C$_6$ alkyl)carbonyl radical; an N-Z-amino(C$_1$–C$_6$ alkyl)carbonyl radical; an N-(C$_1$–C$_6$ alkyl)amino(C$_1$–C$_6$ alkyl)carbonyl radical; and an N,N-di(C$_1$–C$_6$ alkyl)amino(C$_1$–C$_6$ alkyl)carbonyl radical;

Z is chosen from the unsaturated cationic groups of formulae (II) and (III) below and the saturated cationic groups of formula (IV) below:

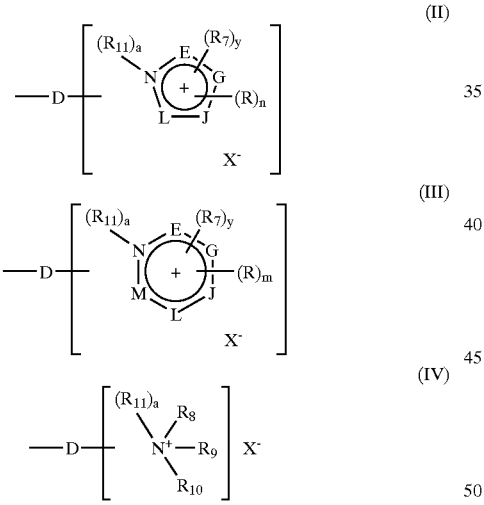

in which:

D is a linker which is chosen from linear and branched alkyl chains and may be interrupted by at least one heteroatom atom and may be substituted by at least one of a hydroxyl and a C$_1$–C$_6$ alkoxy radical, and may carry at least one ketone function;

the ring members E, G, J, L and M, which are identical or different, are chosen from carbon, oxygen, sulphur and nitrogen atoms;

n is an integer ranging from 0 to 4;

m is an integer ranging from 0 to 5;

the radicals R, which are identical or different, may be chosen from a group Z; a halogen atom; a hydroxyl radical; a C$_1$–C$_6$ alkyl radical; a C$_1$–C$_6$ monohydroxyalkyl radical; a C$_2$–C$_6$ polyhydroxyalkyl radical; a nitro radical; a cyano radical; a C$_1$–C$_6$ cyanoalkyl radical; a C$_1$–C$_6$ alkoxy radical; a C$_1$–C$_6$tri(C$_1$–C$_6$ alkyl) silanealkyl radical; an amido radical; an aldehydo radical; a carboxyl radical; a C$_1$–C$_6$ alkylcarbonyl radical; a thio radical; a C$_1$–C$_6$ thioalkyl radical; a (C$_1$–C$_6$ alkyl)thio radical; an amino radical; an amino radical protected by a group chosen from (C$_1$–C$_5$ alkyl) carbonyl, carbamyl, and (C$_1$–C$_6$ alkyl)sulphonyl; and groups NHR" and NR"R'" in which R" and R'", which are identical or different, are chosen from a C$_1$–C$_6$ alkyl radical, a C$_1$–C$_6$ monohydroxyalkyl radical and a C$_2$–C$_6$ polyhydroxyalkyl radical;

R$_7$ is chosen from a C$_1$–C$_6$ alkyl radical; a C$_1$–C$_6$ monohydroxyalkyl radical; a C$_2$–C$_6$ polyhydroxyalkyl radical; a C$_1$–C$_6$ cyanoalkyl radical; a C$_1$–C$_6$ tri(C$_1$–C$_6$ alkyl)silanealkyl radical; a C$_1$–C$_6$ (C$_1$–C$_6$ alkoxy)alkyl radical; a carbamyl(C$_1$–C$_6$ alkyl) radical; a C$_1$–C$_6$ (C$_1$–C$_6$ alkyl)carboxyalkyl radical; a benzyl radical; and a group Z;

R$_8$, R$_9$ and R$_{10}$, which are identical or different, are chosen from a C$_1$–C$_6$ alkyl radical; a C$_1$–C$_6$ monohydroxyalkyl radical; a C$_2$–C$_6$ polyhydroxyalkyl radical; a C$_1$–C$_6$ (C$_1$–C$_6$ alkoxy)alkyl radical; a C$_1$–C$_6$ cyanoalkyl radical; an aryl radical; a benzyl radical; a C$_1$–C$_6$ amidoalkyl radical; a C$_1$–C$_6$ tri(C$_1$–C$_6$ alkyl) silanealkyl radical; and a C$_1$–C$_6$ aminoalkyl radical whose amine is protected by at least one of a (C$_1$–C$_6$ alkyl)carbonyl, amido, carboxyl and (C$_1$–C$_6$ alkyl) sulphonyl radical;

two of the radicals R$_8$, R$_9$ and R$_{10}$ may form, together with the nitrogen to which they are attached, a ring chosen from saturated 5- and 6-membered carbon-containing rings which may contain at least one heteroatom, wherein said rings may contain a substituent chosen from a halogen atom; a hydroxyl radical; a C$_1$–C$_6$ alkyl radical, a C$_1$–C$_6$ monohydroxyalkyl radical; a C$_2$–C$_6$ polyhydroxyalkyl radical; a nitro radical; a cyano radical; a C$_1$–C$_6$ cyanoalkyl radical; a C$_1$–C$_6$ alkoxy radical; a C$_1$–C$_6$ tri(C$_1$–C$_6$ alkyl)silanealkyl radical; an amido radical; an aldehydo radical; a carboxyl radical; a C$_1$–C$_6$ ketoalkyl radical; a thio radical; a C$_1$–C$_6$ thioalkyl radical; a (C$_1$–C$_6$ alkyl)thio radical; an amino radical; and an amino radical protected by a group chosen from (C$_1$–C$_6$ alkyl)carbonyl; carbamyl and (C$_1$–C$_6$ alkyl)sulphonyl radical;

one of the radicals R$_8$, R$_9$ and R$_{10}$ may be chosen from a second group Z, identical to or different from the first group Z;

R$_{11}$ may be chosen from a C$_1$–C$_6$ alkyl radical; a C$_1$–C$_6$ monohydroxyalkyl radical; a C$_2$–C$_6$ polyhydroxyalkyl radical; an aryl radical; a benzyl radical; a C$_1$–C$_6$ aminoalkyl radical; a C$_1$–C$_6$ aminoalkyl radical whose amine is protected by at least one of a (C$_1$–C$_6$ alkyl) carbonyl, a carbamyl, and a (C$_1$–C$_6$ alkyl)sulphonyl radical; a C$_1$–C$_6$ carboxyalkyl radical; a C$_1$–C$_6$ cyanoalkyl radical; a C$_1$–C$_6$ carbamylalkyl radical; a C$_1$–C$_6$ trifluoroalkyl radical; a C$_1$–C$_6$ tri(C$_1$–C$_6$ alkyl) silanealkyl radical; a C$_1$–C$_6$ sulphonamidoalkyl radical; C$_1$–C$_6$ (C$_1$–C$_6$ alkyl)carboxyalkyl radical; a C$_1$–C$_6$ (C$_1$–C$_6$ alkyl)sulphinylalkyl radical; a C$_1$–C$_6$ (C$_1$–C$_6$ alkyl)sulphonylalkyl radical; a C$_1$–C$_6$ (C$_1$–C$_6$ alkyl) ketoalkyl radical; a C$_1$–C$_6$ N-(C$_1$–C$_6$ alkyl) carbamylalkyl radical; and a C$_1$–C$_6$ N-(C$_1$–C$_6$ alkyl) sulphonamidoalkyl radical;

a and y are integers equal to 0 or 1; with the following conditions:

in the unsaturated cationic groups of formula (II):
  when a=0, the linker D is attached to the nitrogen atom,
  when a=1, the linker D is attached to one of the ring members E, G, J or L,
  y can adopt the value 1 only
  1) when the ring members E, G, J and L are simultaneously a carbon atom and when the radical $R_7$ is carried by the nitrogen atom of the unsaturated ring; or
  2) when at least one of the ring members E, G, J and L is chosen from a nitrogen atom to which the radical $R_7$ is attached;
in the unsaturated cationic groups of formula (III):
  when a=0, the linker D is attached to the nitrogen atom,
  when a=1, the linker D is attached to one of the ring members E, G, J, L or M,
  y can adopt the value 1 only
  1) when at least one of the ring members E, G, J, L and M is chosen from a divalent atom and
  2) when the radical $R_7$ is carried by the nitrogen atom of the unsaturated ring;
in the saturated cationic groups of formula (IV):
  when a=0, then the linker D is attached to the nitrogen atom which carries the radicals $R_8$ to $R_{10}$,
  when a=1, then two of the radicals $R_8$ to $R_{10}$, together with the nitrogen atom to which they are attached, form a ring chosen from 5- and 6-membered saturated rings, and the linker D is carried by a carbon atom of the said ring;
$X^-$ is chosen from monovalent and divalent anions;
with the proviso that at least one of $R_1$, $R_2$ and $R_3$ is a group Z.

* * * * *